United States Patent [19]
Goldenberg et al.

[11] Patent Number: 5,470,330
[45] Date of Patent: Nov. 28, 1995

[54] GUIDANCE AND DELIVERY SYSTEM FOR HIGH-ENERGY PULSED LASER LIGHT

[75] Inventors: Tsvi Goldenberg, Irvine; John Wardle, Mission Viejo; William Anderson, Balboa Island, all of Calif.

[73] Assignee: Advanced Interventional Systems, Inc., Irvine, Calif.

[21] Appl. No.: 657,157

[22] Filed: Feb. 19, 1991

Related U.S. Application Data

[63] Continuation-in-part of Ser. No. 593,485, Oct. 3, 1990, Pat. No. 5,188,632, which is a continuation of Ser. No. 218,907, Jul. 14, 1988, abandoned, which is a continuation-in-part of Ser. No. 51,382, May 19, 1987, Pat. No. 4,830,460, which is a continuation-in-part of Ser. No. 860,241, May 6, 1986, Pat. No. 4,799,754, which is a continuation-in-part of Ser. No. 779,844, Sep. 25, 1985, Pat. No. 4,732,448, which is a continuation-in-part of Ser. No. 679,538, Dec. 7, 1984, Pat. No. 4,641,912.

[51] Int. Cl.$^6$ .................................................. A61N 5/02
[52] U.S. Cl. ........................... 606/7; 606/10; 606/15; 606/17
[58] Field of Search ................. 128/772, 654, 128/345, 347–398; 606/7, 10–18

[56] References Cited

U.S. PATENT DOCUMENTS

| Re. 31,289 | 6/1983 | Moore et al. | 128/6 |
|---|---|---|---|
| Re. 31,290 | 6/1983 | Moore et al. | 128/6 |
| 3,327,712 | 6/1967 | Kaufman et al. | 128/398 |
| 3,434,775 | 3/1969 | Gosselin | 355/288 |
| 3,452,742 | 7/1969 | Muller | 128/772 |
| 3,556,085 | 1/1971 | Takahashi | 128/6 |
| 3,920,980 | 11/1975 | Nath | 606/15 |
| 3,922,063 | 11/1975 | Marrone | 350/96 |

(List continued on next page.)

FOREIGN PATENT DOCUMENTS

| 0214712 | 3/1987 | European Pat. Off. . |
|---|---|---|
| 2517019 | 10/1976 | Germany . |
| 59-111125 | 6/1984 | Japan . |
| 59-228602 | 12/1984 | Japan . |
| 1042281 | 9/1966 | United Kingdom . |
| 2095422 | 9/1982 | United Kingdom . |
| WO88/00810 | 2/1988 | WIPO . |

OTHER PUBLICATIONS

*Intraluminal Ultrasound Guidance of Transverse Laser Coronary Atherectomy*, Optical Fibers in Medicine V, Jan. 1990.

Lasers in Surgery and Medicine, 1984, pp. 201–206, "Far–Ultraviolet Laser Ablation of Atherosclerotic Lesions".

*Primary Examiner*—David M. Shay
*Attorney, Agent, or Firm*—Burns, Doane, Swecker & Mathis

[57] ABSTRACT

A deflectable guidewire for a catheter includes a core extending from the proximal end of the guidewire toward the distal end thereof; a hollow sheath for encasing the core; the hollow core including a deflecting region at the distal end of the guidewire, the deflecting region having a first side and a second side, the first side being on an opposite side of a plane extending axially through the hollow means than the second side; the first side of the deflecting region being able to be compressed a greater distance than the second side of the deflecting region; the core being fixed to the hollow sheath at the distal side of the deflecting region; and a control handle mounted at the proximal end of the core and the hollow sheath for applying tension to the core with respect to the hollow sheath so that the tension causes the first side of the deflecting region to compress a greater amount than the second side, thus deflecting the deflecting region. In one embodiment, the core may include laser conducting optical fibers. Other features of the present invention include arranging the optical fibers in the catheter in such a way that bending stresses are distributed evenly throughout the fibers when the catheter is bent. One method of doing this is to arrange the fibers in rows or layers wherein each row or layer is twisted in a direction that is opposite to the direction of the adjacent rows or layers. It has also been found that flexibility is increased without unacceptable transmission losses by using optical fibers having a diameter of about fifty microns.

26 Claims, 23 Drawing Sheets

U.S. PATENT DOCUMENTS

| | | | |
|---|---|---|---|
| 3,987,781 | 10/1976 | Nozik et al. | 126/277 |
| 4,003,369 | 1/1977 | Heilman et al. | 128/770 |
| 4,009,382 | 2/1977 | Nath | 350/96 R |
| 4,011,403 | 3/1977 | Epstein et al. | 350/96 R |
| 4,045,119 | 8/1977 | Eastgate | 350/96 LM |
| 4,170,997 | 10/1979 | Pinnow et al. | 128/6 |
| 4,173,393 | 11/1979 | Maurer | 350/96.34 |
| 4,199,218 | 4/1980 | Steinhage et al. | 350/1.7 |
| 4,207,874 | 6/1980 | Choy | 606/7 |
| 4,215,703 | 8/1980 | Willson | 128/772 |
| 4,221,825 | 9/1980 | Guerder et al. | 350/96.31 |
| 4,244,362 | 1/1981 | Anderson | 128/200.16 |
| 4,248,213 | 2/1981 | Landre | 128/6 |
| 4,266,548 | 5/1981 | Davi | 606/14 |
| 4,270,845 | 6/1981 | Takizawa et al. | 606/19 |
| 4,272,156 | 6/1981 | Ishibashi et al. | 128/6 |
| 4,273,109 | 6/1981 | Enderby | 128/6 |
| 4,286,232 | 8/1981 | Puech et al. | 331/94 |
| 4,305,640 | 12/1981 | Cullis et al. | 350/96.10 |
| 4,331,132 | 5/1982 | Mukasa | 128/6 |
| 4,361,139 | 11/1982 | Takagi | 128/6 |
| 4,367,729 | 1/1983 | Ogiu | 128/6 |
| 4,392,485 | 7/1983 | Hiltebrandt | 128/6 |
| 4,392,715 | 7/1983 | Bonewitz et al. | 350/96.33 |
| 4,398,790 | 8/1983 | Righini et al. | 350/96.18 |
| 4,418,688 | 12/1983 | Loeb | 606/7 |
| 4,418,689 | 12/1983 | Kanazawa | 128/6 |
| 4,419,987 | 12/1983 | Ogiu | 128/6 |
| 4,445,754 | 5/1984 | Beales et al. | 350/96.34 |
| 4,456,017 | 6/1984 | Miles | 128/772 |
| 4,490,020 | 12/1984 | Sakaguchi et al. | 350/96.18 |
| 4,504,114 | 3/1985 | Arrington | 350/96.34 |
| 4,511,209 | 4/1985 | Skutnik | 350/96.34 |
| 4,521,070 | 6/1985 | Sottini et al. | 350/96.15 |
| 4,526,170 | 7/1985 | Tanner | 606/14 |
| 4,565,197 | 1/1986 | Daly | 606/4 |
| 4,569,335 | 2/1986 | Tsuno | 128/6 |
| 4,576,177 | 3/1986 | Webster, Jr. | 606/7 |
| 4,576,435 | 3/1986 | Nishioka | 128/395 |
| 4,583,539 | 4/1986 | Karlin et al. | 606/4 |
| 4,627,436 | 12/1986 | Leckrone | 606/7 |
| 4,641,912 | 2/1987 | Goldenberg | 606/7 |
| 4,652,083 | 3/1987 | Laakmann | 350/96.32 |
| 4,657,014 | 4/1987 | Edelman et al. | 606/15 |
| 4,672,961 | 6/1987 | Davies | 606/7 |
| 4,681,104 | 7/1987 | Edelman | 606/17 |
| 4,681,351 | 7/1987 | Bartholomew | 285/319 |
| 4,681,396 | 7/1987 | Jones | 350/96.18 |
| 4,686,963 | 8/1987 | Cohen et al. | 128/6 |
| 4,686,979 | 8/1987 | Gwen et al. | 128/397 |
| 4,729,384 | 3/1988 | Bagenet | 128/772 |
| 4,729,621 | 3/1988 | Edelman | 604/21 |
| 4,732,448 | 3/1988 | Goldenberg | 606/7 |
| 4,748,986 | 6/1988 | Morrison et al. | 128/772 |
| 4,784,132 | 11/1988 | Fox et al. | 606/7 |
| 4,800,876 | 1/1989 | Fox et al. | 606/7 |
| 4,819,632 | 4/1989 | Davies | 606/7 |
| 4,821,731 | 4/1989 | Martinelli et al. | 128/662.06 |
| 4,832,023 | 5/1989 | Murphy-Chutorian | 606/7 |
| 4,848,336 | 7/1989 | Fox et al. | 606/7 |
| 4,862,893 | 9/1989 | Martinelli | 128/662.03 |
| 4,886,067 | 12/1989 | Palermo | 128/772 |
| 5,055,109 | 10/1991 | Gould et al. | 604/95 |
| 5,060,660 | 10/1991 | Gambale et al. | 128/772 |
| 5,067,489 | 11/1991 | Lind | 128/772 |
| 5,069,217 | 12/1991 | Fleischhacker, Jr. | 128/657 |
| 5,069,226 | 12/1991 | Yamauchi et al. | 128/772 |

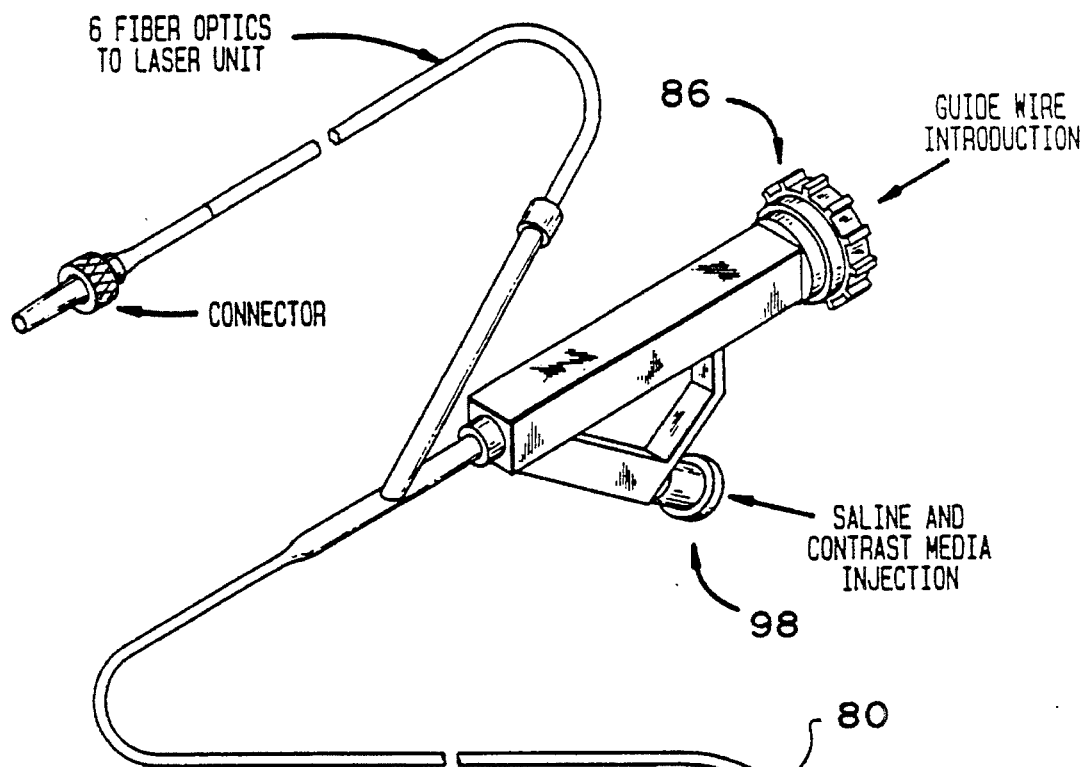
FIG. 6
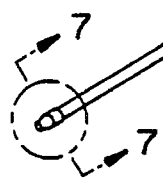
FIG. 8
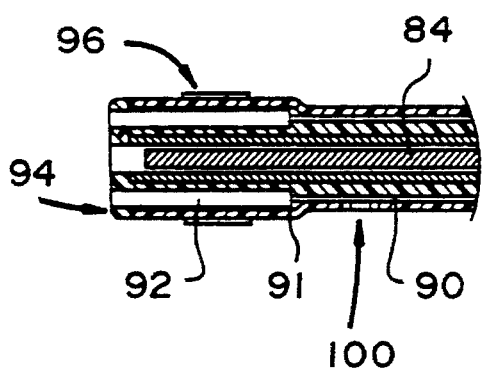
FIG. 7
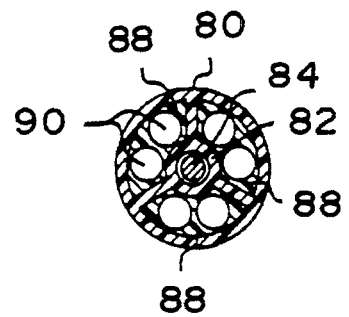

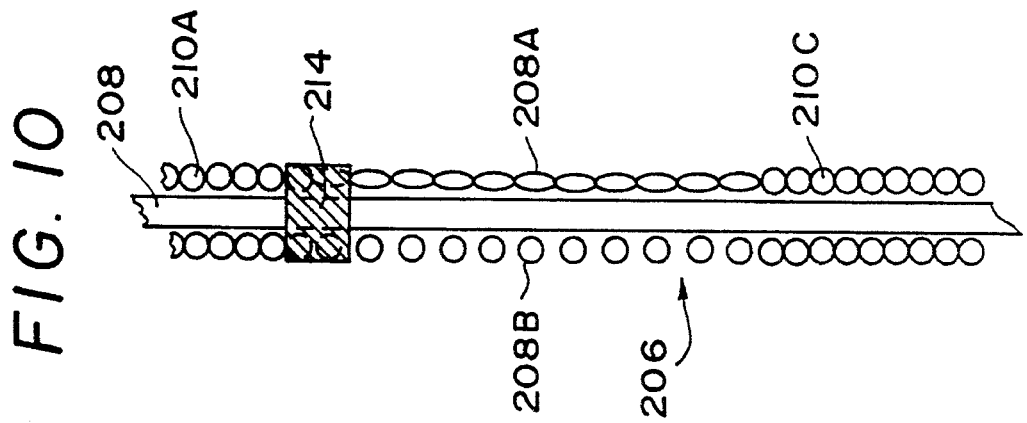
FIG. 10
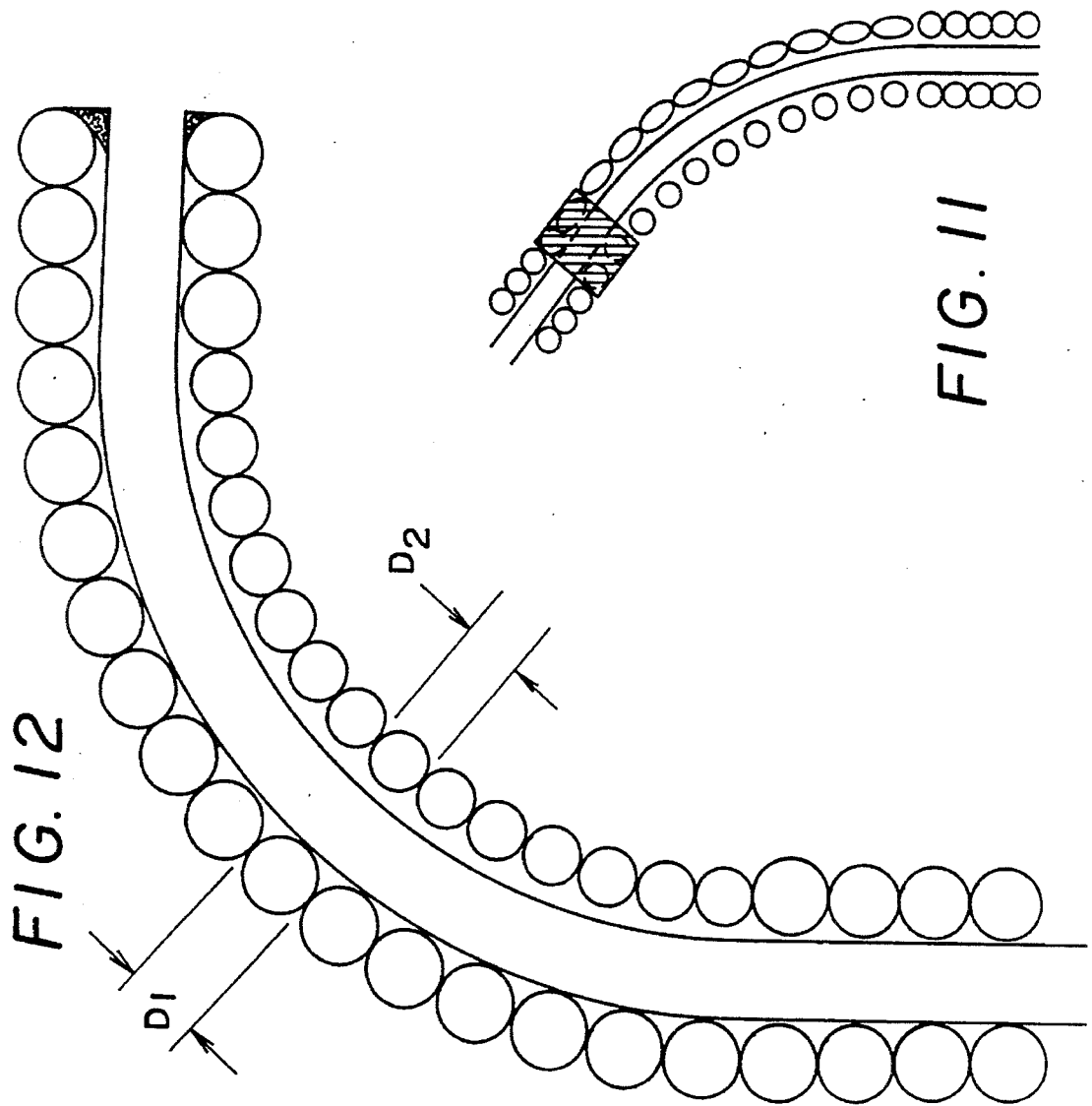
FIG. 11
FIG. 12

PRIOR ART

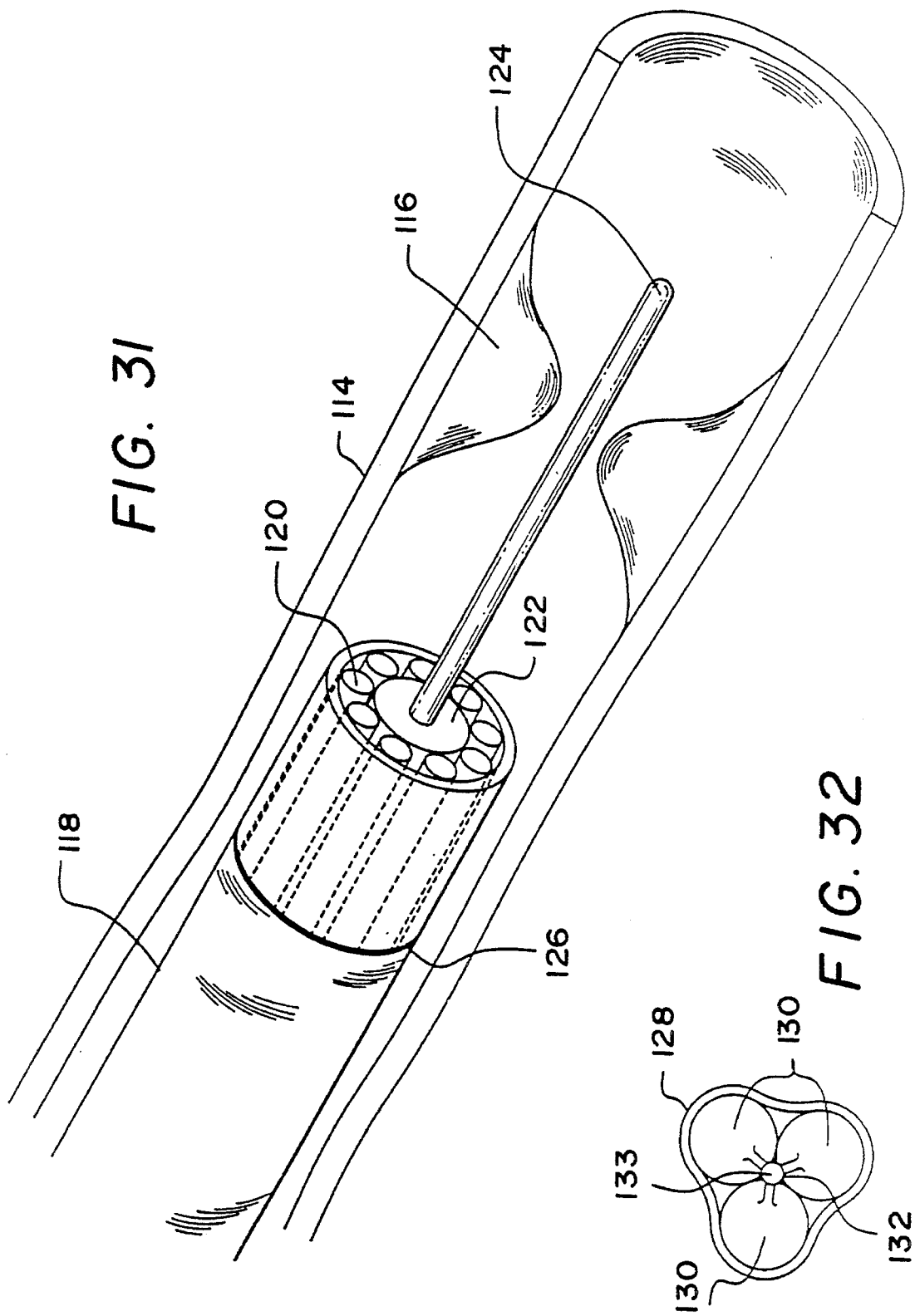

GUIDANCE AND DELIVERY SYSTEM FOR HIGH-ENERGY PULSED LASER LIGHT

CROSS-REFERENCE TO RELATED APPLICATIONS

This is a continuation-in-part of application Ser. No. 07/593,485, filed Oct. 3, 1990, now U.S. Pat. No. 5,188,632, which is a continuation of application Ser. No. 07/218,907, filed on Jul. 14, 1988 (now abandoned); which was a continuation-in-part of application Ser. No. 07/051,382, filed on May 19, 1987, now U.S. Pat. No. 4,830,460; which is a continuation-in-part of application Ser. No. 06/860,241, filed on May 6, 1986, now U.S. Pat. No. 4,799,754; which is a continuation-in-part of application Ser. No. 06/779,844, filed on Sept. 25, 1985, now U.S. Pat. No. 4,732,448; which is a continuation-in-part of application Ser. No. 06/679,538, filed on Dec. 7, 1984, now U.S. Pat. No. 4,641,912; the disclosures of which are herein incorporated by reference thereto.

BACKGROUND OF THE INVENTION

The present invention is directed to a system for delivering high energy laser light by means of an optical waveguide, and in one particular application is concerned with laser angioplasty and a means for guiding such a system.

The use of laser energy to ablate atherosclerotic plaque that forms an obstruction in a blood vessel is presently being investigated as a viable alternative to coronary bypass surgery. This procedure, known as angioplasty, essentially involves insertion of a fiber optic waveguide into the vessel, and conduction of laser energy through the waveguide to direct it at the plaque once the distal end of the waveguide is positioned adjacent the obstruction. In certain uses, to enable the physician to ascertain the location of the waveguide as it is being moved through the vessel, additional waveguides for providing a source of illuminating light and for conducting the image from inside the vessel to the physician are fed together with the laser waveguide.

Most of the experimentation and testing that has been done in this area has utilized continuous wave laser energy, such as that produced by Argon Ion, Nd:YAG or Carbon Dioxide lasers. The light produced by this type of laser is at a relatively low energy level. Ablation of the obstruction is achieved with these types of lasers by heating the plaque with constant laser power over a period of time until the temperature is great enough to destroy it.

While the use of continuous wave laser energy has been found to be sufficient to ablate an obstruction, it is not without its drawbacks. Most significantly, the destruction of the lesion is uncontrolled and is accompanied by thermal injury to the vessel walls immediately adjacent the obstruction. In an effort to avoid such thermal injury and to provide better control of the tissue removal, the use of a different, higher level form of laser energy having a wavelength in the ultra-violet range (40-400 nanometers) has been suggested. See, for example, International Patent Application PCT/US84/02000, published Jun. 20, 1985. One example of a laser for producing this higher level energy is known as the Excimer laser, which employs a laser medium such as argon-chloride having a wavelength of 193 nanometers, krypton-chloride (222 nm), krypton-fluoride (248 nm), xenon-chloride (308 nm) or xenon-fluorine (351 nm). The light produced by this type of laser appears in short bursts or pulses that typically last in the range of ten to hundreds of nanoseconds and have a high peak energy level, for example as much as 200 mJ.

Although the destruction mechanism involving this form of energy is not completely understood, it has been observed that each single pulse of the Excimer laser produces an incision which destroys the target tissue without accompanying thermal injury to the surrounding area. This result has been theorized to be due to either or both of two phenomena. The delivery of the short duration, high energy pulses may vaporize the material so rapidly that heat transfer to the nonirradiated adjacent tissue is minimal. Alternatively, or in addition, ultraviolet photons absorbed in the organic material might disrupt molecular bonds to remove tissue by photochemical rather than thermal mechanisms.

While the high peak energy provided by Excimer and other pulsed lasers has been shown to provide improved results with regard to the ablation of atherosclerotic plaque, this characteristic of the energy also presents a serious practical problem. Typically, to couple a large-diameter laser beam into a smaller diameter fiber, the fiber input end is ground and polished to an optical grade flat surface. Residual impurities from the polishing compound and small scratches on the surface absorb the laser energy. These small imperfections result in localized expansion at the surface of the fiber when the laser energy is absorbed. The high-energy Excimer laser pulses contribute to high shear stresses which destroy the integrity of the fiber surface. Continued application of the laser energy causes a deep crater to be formed inside the fiber. Thus, it is not possible to deliver a laser pulse having sufficient energy to ablate tissue in vivo using a conventional system designed for continuous wave laser energy.

This problem associated with the delivery of high energy laser pulses is particularly exacerbated in the field of coronary angioplasty because of the small diameter optical fibers that must be used. For example, a coronary artery typically has an internal diameter of two millimeters or less. Accordingly, the total external diameter of the angioplasty system must be below two millimeters. If this system is composed of three separate optical fibers arranged adjacent one another, it will be appreciated that each individual fiber must be quite small in cross-sectional area.

A critical parameter with regard to the destruction of an optical fiber is the density of the energy that is presented to the end of the fiber. In order to successfully deliver the laser energy, the energy density must be maintained below the destruction threshold of the fiber. Thus, it will be appreciated that fibers having a small cross-sectional area, such as those used in angioplasty, can conduct only a limited amount of energy if the density level is maintained below the threshold value. This limited amount of energy may not be sufficient to efficiently ablate the obstructing tissue or plaque without thermal damage.

Even if the energy density is quite high, the small beam that results from the small diameter fiber may not have a sufficiently large target area that effective ablation of the lesion results. Only a small fragment of the lesion might be ablated, and thus not provide adequate relief from the blockage. A further problem with the use of a fiber optic waveguide to direct laser energy for purposes of ablating atherosclerotic plaque is that of perforation of the blood vessel. Such perforations can be caused by the waveguide itself contacting and perforating the vessel. Such perforations can also be caused by the laser beam, particularly if the waveguide is not aligned properly within the blood vessel. The perforation problems are related to the intrinsic stiffness of the glass fibers of the waveguide and poor control of laser energy, regardless of laser source or wavelength.

Also related to the stiffness of the glass fibers is the ability to control the position of the fibers radially within the blood vessels. The conventional systems employing fiber optic waveguides within a blood vessel do not provide means for controlling radial movement within the blood vessel.

One known attempt at developing an angioplasty catheter is disclosed in U.S. Pat. No. 4,747,405. The known catheter includes a center guidewire lumen, a guidewire therein, and a single optical fiber disposed at a side of the catheter for emitting laser energy. The catheter also has a blunt leading end that does not facilitate progress through a blood vessel. A particular problem that potentially results from the disclosed arrangement of the single optical fiber and guidewire is that large segments of the lesion may become loose in the blood stream and could possibly cause an emboli. As a result, the known catheter includes a dedicated channel to remove the loosened debris.

Currently "over the wire" laser catheters are guided through coronary arteries with nondeflectable guidewires. In a laser angioplasty procedure, the physician first introduces the guidewire into the blood vessel where treatment is required. The catheter is then tracked over the guidewire and the laser is activated as required to treat the vessel. Because plaque is frequently built up eccentrically within the vessel, it is frequently desirable during a procedure to change the general direction of the guidewire, and thus the path of the catheter within the vessel. With a nondeflectable guidewire, it can be difficult to change the direction of the guidewire.

Laser angioplasty systems for the treatment of nontotal occlusions include systems that have a bundle of fibers placed concentrically around a guidewire lumen, and which are covered in a protective sheath. Small diameter catheters, e.g., 1.0 to 1.7 mm O.D., have a ring of active optical fibers that extends from the center guidewire lumen to the outer protective sheath. Any occlusive material confronted by the advancing catheter will be removed by the active fiber ring.

These small diameter catheters contain fewer fibers than large diameter catheters, e.g., 1.8 mm O.D. and greater. With the increased number of optical fibers in the large diameter catheters, catheter flexibility is reduced, thus making the catheter more difficult to use. However, large arteries require a large diameter catheter.

Efforts to guide catheters by means of ultrasonic transducers are taught in U.S. Pat. Nos. 4,576,177; 4,821,731; and 4,862,893; as well as in an article titled Intraluminal Ultrasound Guidance of Transverse Laser Coronary Atherectomy by M. A. Martinelli et al.

OBJECTS AND BRIEF STATEMENT OF THE INVENTION

Accordingly, it is a general object of the invention to provide a novel system for delivering high energy pulsed laser light using an optical waveguide.

It is a more specific object of the invention to provide such a delivery system that is particularly well suited to deliver ultraviolet laser energy in vivo for the ablation of atherosclerotic plaque. In this regard, it is a particular object of the present invention to provide a highly efficient waveguide for use in such a delivery system.

It is yet another object of the present invention to provide such a delivery system that is adapted to minimize the likelihood of perforating or otherwise damaging a blood vessel in which the system is being used.

It is a further object of the present invention to provide such a system that includes a guide for facilitating the maneuvering of the optical waveguides through the blood vessel in which the system is being used.

It is another object of the present invention to provide a device for controlling the radial movement of the optical waveguide within the blood vessel in which the system is being used.

It is another object of the present invention to overcome the aforementioned problems associated with the use of nondeflectable guidewires. In this regard, one aspect of a delivery system embodying the present invention relates to a guidance system that facilitates guiding an optical fiber system through a blood vessel. In one embodiment, the guidance system comprises a guidewire in which the distal tip thereof may be deflected by a mechanism that is controlled by an operator at the proximal end thereof. Such a mechanism includes a wire coil surrounding a center core. At some position along the coil, preferably the distal end, the wire is shaped in a nonuniform manner such that the diameter or width of the wire in the coil is smaller on one side of the guidewire than it is on the other side of the guidewire. The center core is fixed to the wire coil at the distal end of the nonuniform portion. At the proximal end of the guidewire, a deflection handle is provided that is able to provide tension on the core with respect to the wire coil so as to cause the wire coil to compress unevenly at the nonuniform section thereof. The uneven compression causes the coil, and thus the distal end of the guidewire to deflect.

In another embodiment, the above-described mechanism for deflecting a guidewire is used in conjunction with a fiber optic catheter as the core. An ultrasound system is also used to facilitate guiding the catheter. In such an embodiment, the wire coil, which includes an uneven portion therein, is positioned about a fiber optic bundle. Ultrasound sensors are provided at the distal end of the system for providing information to the operator. In a further variation of this embodiment, a radiopaque band, which functions as an x-ray opaque marker, is used with the ultrasound sensors.

In another embodiment of the present invention, the flexibility of large diameter catheters is enhanced by the utilization of a specially designed catheter and guidewire. The catheter comprises a central lumen for accommodating a guidewire. A concentric lumen surrounds the guidewire lumen and includes a plurality of optical fibers for carrying laser energy to the distal end of the catheter. In order to increase the effective ablating area of the catheter, while minimizing ischemia, the catheter has an expanded distal tip portion that increases the effective outer diameter of the ring of active optical fibers. However, in order to reduce the number of optical fibers needed to fill the ring of optical fibers, and thus increase the flexibility of the catheter, the guidewire lumen is similarly expanded at the distal tip. The guidewire also has an enlarged distal tip that fits within the expanded portion of the guidewire lumen. Such an arrangement enables the guidewire to center the catheter with respect to an occlusion, keeps the distal tip of the catheter collinear to the occluded vessel, and displaces occlusive material in an outward radial direction as it is advanced.

Other features of the present invention include arranging the optical fibers in the catheter in such a way that bending stresses are distributed evenly throughout the fibers when the catheter is bent. One method of doing this is to arrange the fibers in rows or layers wherein each row or layer is twisted in a direction that is opposite to the direction of the adjacent rows or layers.

It has also been found that flexibility is increased without jeopardizing transmission losses by using optical fibers having a diameter of about fifty microns.

In yet another embodiment of the present invention, an eccentric guidewire lumen includes a fountain pen-like tip that forms a leading point of the catheter. The optical fibers are also arranged in a manner that conforms to the shape of the tip.

In another embodiment of the present invention, a balloon is used to lock an outer catheter to a vessel wall while an inner catheter advances through the vessel to ablate a lesion therein.

BRIEF DESCRIPTION OF THE DRAWINGS

FIG. 6 is a perspective view of an alternative embodiment of a multilumen, multifiber catheter;

FIG. 7 is a cross-sectional end view of the distal portion of the catheter of FIG. 6;

FIG. 8 is an enlarged cross-sectional side view of the catheter of FIG. 6;

FIG. 10 is a view of the embodiment of FIG. 9 in a nondeflected position;

FIG. 11 is a view of the embodiment of FIG. 9 in a deflected position;

FIG. 12 is an alternative of the embodiment of FIG. 9;

FIG. 31 is a perspective view of an alternative embodiment of a large-area ablation catheter which employs multiple fibers;

FIG. 32 is an end view of an embodiment of a catheter which employs balloons for displacing a fiber optic waveguide in a blood vessel;

DESCRIPTION OF THE ILLUSTRATED EMBODIMENTS

In the following specification, a laser delivery system is described with particular reference to the use of a high energy pulsed laser, such as an Excimer laser, in an angioplasty system, to facilitate an understanding of the invention and its uses.

Figure 1:
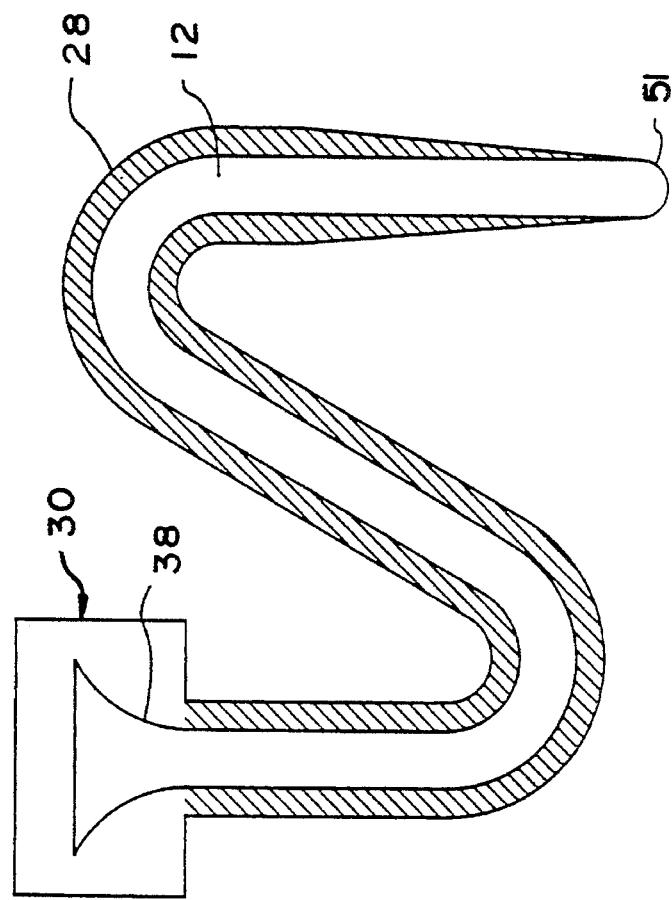
FIG. 1 is a cross-sectional side view of a delivery system for high energy Excimer laser light utilizing a funnel-shaped energy coupler.

Referring now to FIG. 1, one embodiment of the delivery system for high energy pulsed laser light is illustrated in greater detail. The delivery system comprises two basic elements. One of these is the optical fiber 12, and the other is the energy coupler 30. A fiber that is particularly suitable for use in the delivery of high energy pulsed ultraviolet laser light is a multi-mode fiber which has a relatively large core, or active area, relative to the area of its cladding, i.e., the outer skin of the fiber. The core is made of substantially pure synthetic fused silica, i.e., amorphous silicon dioxide. This material preferably has a metallic impurity content of no more than 30 parts per million, to provide better conduction of the transmitted laser energy than that which is obtainable with natural fused quartz. The term "metallic impurity" includes both, metals per se and oxides thereof.

Even with such a low level of metallic impurity, defects in the silica fiber can serve as linear and non-linear absorption sites for the photons. These defects can vary from oxygen vacancy to unbonded silicon atoms found in any silica glass. They can result in lowered transmittance of ultraviolet radiation. Increasing the intensity (or energy) of the laser light that is introduced into one end of a fiber exhibiting such defects will not necessarily result in proportionally increased output at the other end. Rather, the increased intensity level can reduce the threshold level at which bulk damage occurs to the silica glass, and thereby destroys the delivery system.

In accordance with one aspect of the present invention, the transmittance of high energy UV laser light in a fiber made of synthetic silica is enhanced by lightly doping the silica with a material which functions to repair some of the inherent structural defects of the silica. The silica is preferably doped with an OH— radical, to thereby form so-called "wet" silica. It is believed that defects in silica that affect UV light transmission comprise oxygen hole centers and unbonded silica atoms. It is theorized that the doping of the silica with the OH- radical functions to repair these defects by eliminating the oxygen holes or vacancies in one case and by bonding to the silicon to form the $SiO_2$ double bond. It has been reported that pure silica having only about 5 parts per million (ppM) of an OH radical has an absorption coefficient which is 2–3 times greater than silica having about 1200 ppM of the radical. See J. H. Stathes et al, *Physical Review B.*, Vol. 29, 12, 1984, pp. 70–79. Other investigations have reported that an optical absorption band appears in silica fibers having a low OH— content as a result of the fiber drawing process. See Kaiser et al, *J. Opt. Soc. Am.*, 63, 1973, p. 1141 and *J. Opt. Soc. Am.* 63, 1974, p. 1765. Apparently, an increase in the OH— content of silica reduces both types of absorption sites described above, and in accordance with the present invention this concept is applied to a system for delivering high peak energy ultraviolet laser pulses to thereby enhance the efficiency of the energy transmittance. Preferably, the silica that makes up the fibers contains about 200 to 2000 ppM of the OH— radical, most preferably 1200 ppM.

In another embodiment of the invention, the silica that is used to produce the fibers of the delivery system is doped with fluorine. Fluorine doped silica exhibits even lower attenuation than high OH silica. It appears that the fluorine functions to shift the absorption band gap in the $SiO_2$ structure, to facilitate the transmittance of a large number of photons at low wavelengths. For multimode fibers having diameters in the range of 100 micrometers to 1500 micrometers, the silica preferably should contain between 0.25 and 2.0 wt % fluorine, most preferably 1.0 wt %.

As a further feature of the invention, the silica can be doped with both the OH— radical and fluorine. When both of these materials are used in combination, the OH radical content should range between 200 and 2000 ppM, and the fluorine should comprise between 0.5 and 3 wt % of the silica.

In the context of the present invention, the fiber can be a single fiber or a bundle of fibers having a total diameter in the range of 100–2,000 microns. A bundle of close-packed small-diameter fibers is preferred because they provide greater overall flexibility and thereby more easily accommodate the twists and tight turns that are required to feed the delivery system through body cavities. This is particularly desirable where a larger diameter waveguide is required to deliver a relatively large diameter beam with uniform intensity, such as in vascular angioplasty. This entire structure can be surrounded by a protective flexible jacket 28 made of a material which is not damaged by ultraviolet light. More particularly, when the fiber undergoes sharp bends, for example at the juncture of two arteries, light losses occur.

These losses may be enough to melt some types of jacket materials such as silicone and nylon. However, UV light resistant materials, for example UV cured acrylate compound or TEFLON®, can sustain high bending losses without degradation and are therefore more desirable for the jacket.

In a preferred form of the invention, the protective jacket is incorporated as part of the fiber itself, rather than being a separate piece of structure which surrounds all of the fibers. As noted previously, every fiber comprises a core and a cladding which surrounds the core to maintain the transmitted light energy within the core. The cross-sectional area of the fiber might normally have a core/cladding ratio of 80/20 to provide suitable flexibility. Typically, both the core and the cladding are made of glass, with the cladding being appropriately modified (e.g., doped) to provide it with a lower index of refraction. In this conventional structure, the protective jacket comprises a third layer which surrounds the core and cladding.

In accordance with one aspect of the invention, the conventional glass cladding is eliminated and the core of the fiber is directly surrounded by a coating of organic material. One specific preferred material is UV-cured acrylate. It has a lower index of refraction than silica, and thereby functions to maintain the laser energy within the core. It also serves to protect the silica glass, and hence eliminates the need for a third layer. This reduces the overall size of the fiber and hence enables the net cross-sectional area of the core to be increased for a delivery system having a given outer diameter.

Further details regarding the composition of preferred coatings can be found in U.S. Pat. No. 4,511,209, the disclosure of which is incorporated herein by reference.

By limiting the coating of the fiber to about 10% of the diameter of the fiber and by keeping the coating arranged substantially uniformly about the fiber, the fibers can be made as small as 50 microns in diameter. Such a fiber is approximately 16 times as flexible as a fiber having a diameter of 100 microns. Accordingly, the multi-fiber catheters described herein can be used with 50µ optical fibers for increased flexibility and limited transmission losses.

A silica fiber of this construction can typically accommodate input energy up to a level around 30 $Mj/mm^2$ produced by a commercially available Excimer laser with a 10–40 pulse. If the density of the energy is increased above this level, the input end of a conventional fiber having a planar, polished surface will be damaged or destroyed if the laser is applied directly to it. Unfortunately, this density level is about the minimum that is required to produce ablation of calcified plaque, thus providing no tolerance range if the intended use of the delivery system is for angioplasty. Accordingly, to enable a higher level of energy to be conducted in the fiber, an energy coupler 38 can be provided at the input end of the fiber. See FIG. 1. In this embodiment, the energy coupler comprises a section of fiber that has a larger cross-sectional area than the main portion of the fiber. This larger cross-sectional area gradually tapers to the nominal diameter of the fiber, to provide a funnel-shaped input section.

Production of such a shape on the end of the fiber can be accomplished by appropriate design of the die through which the silica is drawn to produce the fiber. By interrupting the drawing of the fiber, a bulbous mass remains at one end of the fiber. This mass can be cut and polished to produce the funnel-shaped input section.

In operation, the increased area of the funnel-shaped coupler decreases the input energy density for a given level of energy within the fiber. Accordingly, the area of the input end can be appropriately dimensioned to enable a sufficient amount of energy for ablation of tissue to be coupled into the fiber without damaging the input end. Once it has been coupled in, the density of the energy is increased by decreasing the cross-sectional area of the fiber within the tapered section, so that a greater amount of energy can be conducted within the fiber than would be possible without such a device.

Figure 2:
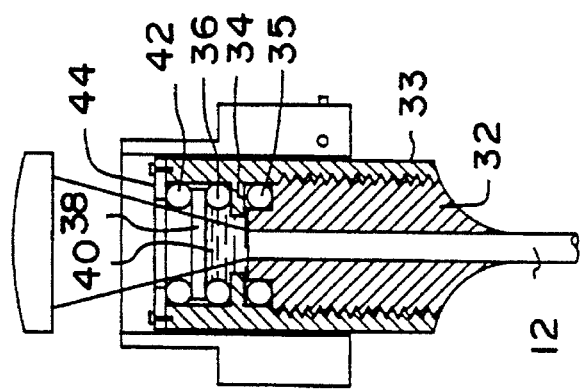
FIG. 2 is a cross-sectional side view of a second embodiment of an energy coupler.

A second embodiment of an energy coupler is illustrated in FIG. 2. In this embodiment, the optical fiber has a uniform diameter along its length and terminates at a flat polished end. The end section of the fiber is encased within a ferrule 32 made of a suitable material such as brass, for example. An aluminum casing 33 having an annular ring 34 projecting from the inner wall thereof is threaded onto the ferrule. A TEFLON® O-ring 35 disposed between the end of the annular ring and the ferrule provides a watertight seal between the casing and the ferrule. A second O-ring 36 is disposed on top of the annular ring and supports a glass plate 38 made of z-cut quartz, for example. This arrangement forms a fluid-tight cavity 40 between the ferrule 32, the casing 33 and the glass plate 38. The glass plate can be held in place by means of a third O-ring 42 and a clamping ring 44 disposed on the top of the casing. The fluid tight cavity is filled with liquid which acts as a buffer to the input end of the fiber, enabling laser energy having a relatively high density to be coupled into the fiber without damage thereto. The liquid within the cavity can be distilled and deionized water, or it can be a transparent oil having an index of refraction that is matched to that of the fiber 12.

Figure 3A:
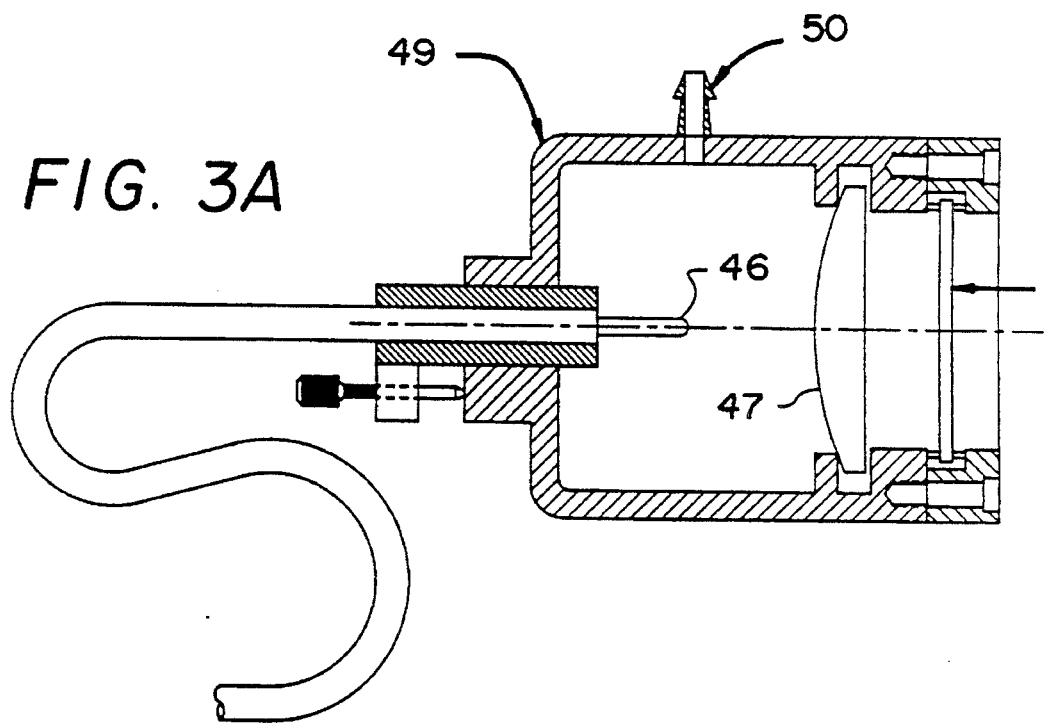
FIG. 3A is a side view, partly in section, of a third embodiment of an energy coupler.
Figure 3B:
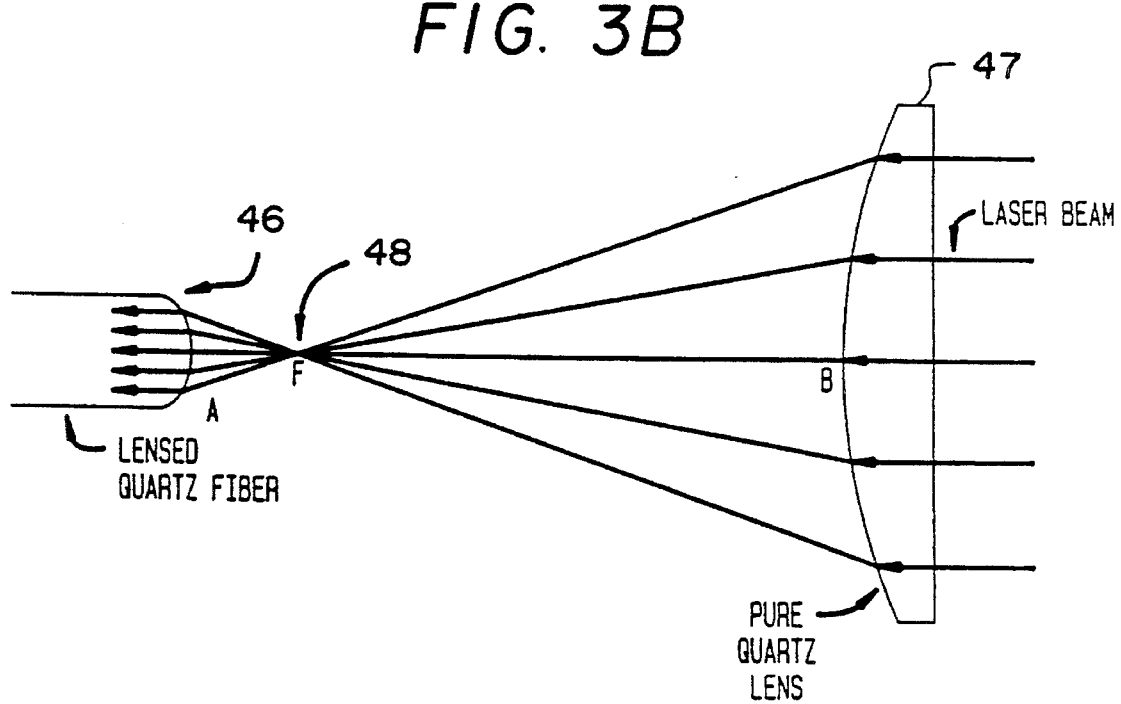
FIG. 3B is an enlarged view of a portion of FIG. 3A, illustrating the principle of operation of this embodiment.

A third embodiment of an energy coupler is illustrated in FIGS. 3A and 3B. In this embodiment, the input end of the fiber is provided with a fused semispherical lens 46. This lens can be formed by melting the material of the fiber itself with a micro-torch, to produce a high purity silica lens with no impurities or cracks. Alternatively, the lens 46 can be a separately ground lens that is attached to the flat end of the fiber. The fiber 12 can be tapered as shown in FIG. 1, or it can have a uniform diameter along its length.

A second lens, preferably a plano-convex lens 47, focuses the input beam from the laser to a focal point 48. The input lens 46 on the fiber is axially aligned with the lens 47 and is located at a distance from the lens 47 which is greater than the focal length of that lens. Thus, the focused laser energy appears to be coming from a point source. The lens 46 collimates this focused energy and couples it into the fiber.

The input end of the fiber with the lens 46 and the focusing lens 47 are housed within a chamber 49. This chamber is provided with a vacuum port 50 to enable the chamber to be evacuated of air. If air were present between the lenses 46 and 47, the highly concentrated energy at the focal point 48 might cause a breakdown of nitrogen and oxygen gases that could contaminate the lens 46. In addition, the vacuum environment keeps out dust and other particles which could settle on the lens 46 and act as a heat sink, destroying the roundness of the lens. Alternatively, this chamber 49 can be filled with a liquid, such as water or oil, for example, which matches the index of refraction of the silica fiber. The higher index of refraction of the liquid reduces the dielectric shock when the pulse propagates from the liquid transmission medium to the fiber, relative to that which is experienced when air is the transmission medium.

Although the preferred embodiment employs a curved lens at the proximal input end of the fiber, it is possible to couple the energy into a fiber having a planar input surface. However, it is important to ensure that this surface is free of scratches and other imperfections. This can be accomplished by heating the end of the fiber with a micro-torch to cause the fiber material to melt and flow slightly, thereby removing the imperfections caused by polishing.

The type of energy coupler shown in FIG. 3A serves to amplify the energy within the fiber. More particularly, the amplification factor is equal to the ratio of the diameter of the laser beam at the lens 47 to the diameter of the fiber. This ratio is also related to the magnification produced by the two lenses. Referring to FIG. 3B, the dimension FB is the focal length of the lens 47 and the dimension FA is the distance between the lens 47 and the focal point 48. The magnification factor of these two lenses is defined as FB/FA. Since this factor must be equal to the laser energy amplification, the appropriate distance between the lenses 46 and 47, i.e., AB=FB FA, can be determined from the following relationship:

$$\frac{FB}{FA} = \frac{D_L}{D_F}$$

where $D_L$ is the diameter of the laser beam and $D_F$ is the diameter of the fiber.

Although illustrated as a separate element in the figures, it will be appreciated that the energy couplers could be incorporated into the structure of a laser, to provide an integrated laser and coupling system.

Thus, with the combination of the lightly doped synthetic silica fiber and the energy coupler 30 that enables a greater level of energy to be conducted through the fiber, an amount of high energy laser light that is sufficient to produce an incision can be safely transmitted through an optical fiber waveguide without the risk of damage to the fiber.

To further increase the peak energy that is delivered through the system, it is preferable to slightly increase the length of the pulses beyond the relatively short duration that is typically produced by commercial Excimer lasers and the like. For example, a pulse having a duration in the range of 10–3000 nsec, more preferably 30–1000 nsec, or 100–300 nsec, enables much higher peak energy to be applied with the same delivery system than a shorter pulse, yet is still sufficiently short to produce the desired cutting action.

One example of a circuit for stretching the output pulses of a laser is the magnetic switch developed at the Jet Propulsion Laboratory by Drs. J. Ladunslager and T. Tacala. In this regard, it is not necessary that each lengthened or stretched pulse comprise a single, continuous pulse. Rather, it could comprise a burst of shorter length successive pulses which together provide an effective pulse length of the desired duration. With the increased energy that is provided by the lengthened pulses, the energy level within the fiber will likely be more than sufficient to enable the laser beam to ablate an obstruction. In fact, the beam could be expanded as it exits the fiber and still contain sufficient energy density to ablate tissue. By expanding the diameter of the laser beam, for example by means of an increasing taper or fusing a larger diameter fiber at the distal end of the fiber, a larger area of tissue is ablated to produce more favorable results towards obtaining better blood flow in a blood vessel while using a small diameter flexible fiber that can be easily propagated through the vessel.

Figure 4:
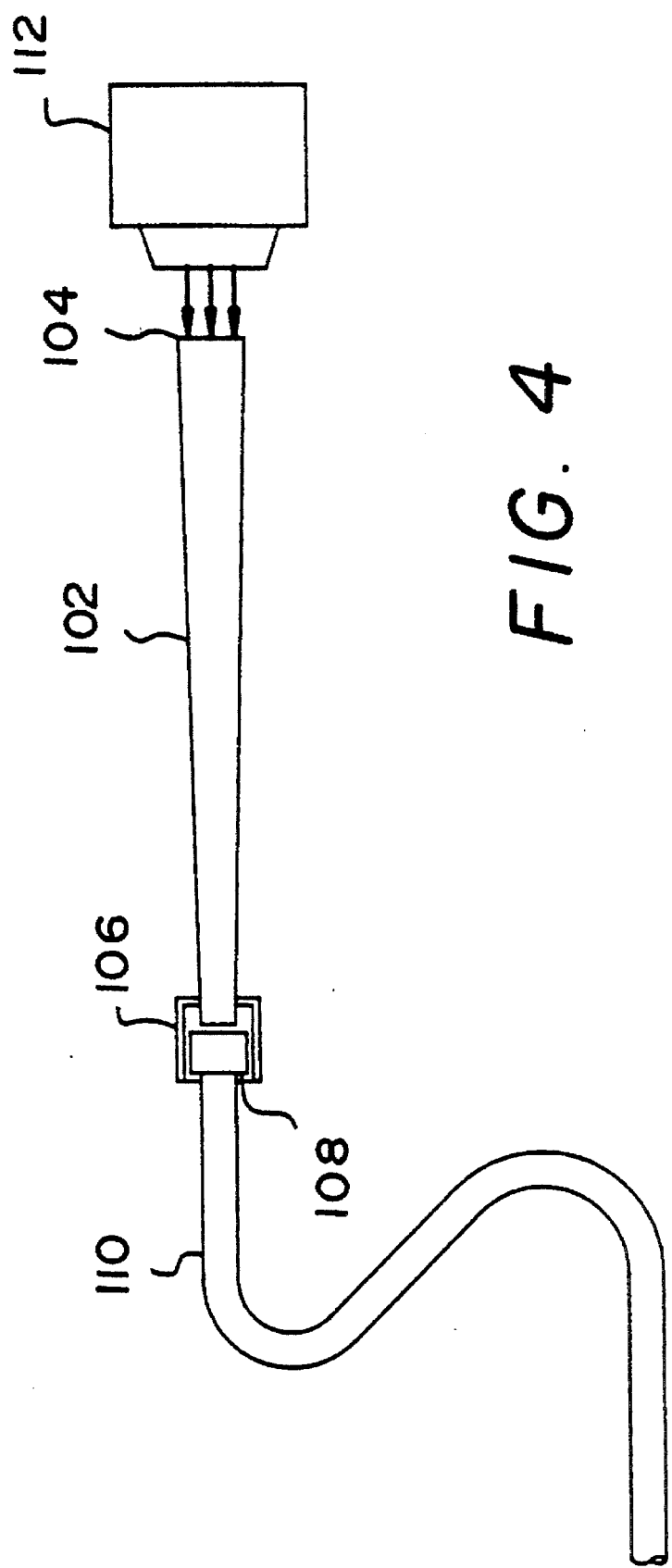
FIG. 4 is a perspective view of an energy coupler according to the present invention.

An additional method of coupling a substantially pure silica fiber delivery system to a high energy pulsed laser, an energy coupler as illustrated in FIG. 4 may be used. A pure silica fiber 102 is tapered at about a one degree (1°) taper and is about 30 centimeters long. The fiber 102 has an input end 104 with a diameter of about 15 mm. At the narrow end 106 of the fiber 102 is a modular connector 106 that connects with a connector 108 on the end of an optical waveguide 110.

A source 112 of laser energy propagates laser energy into the tapered fiber 102 such that, in a preferred embodiment the energy density at the connector 106 is about 50–100 milliJoules/mm$^2$.

Figure 5:
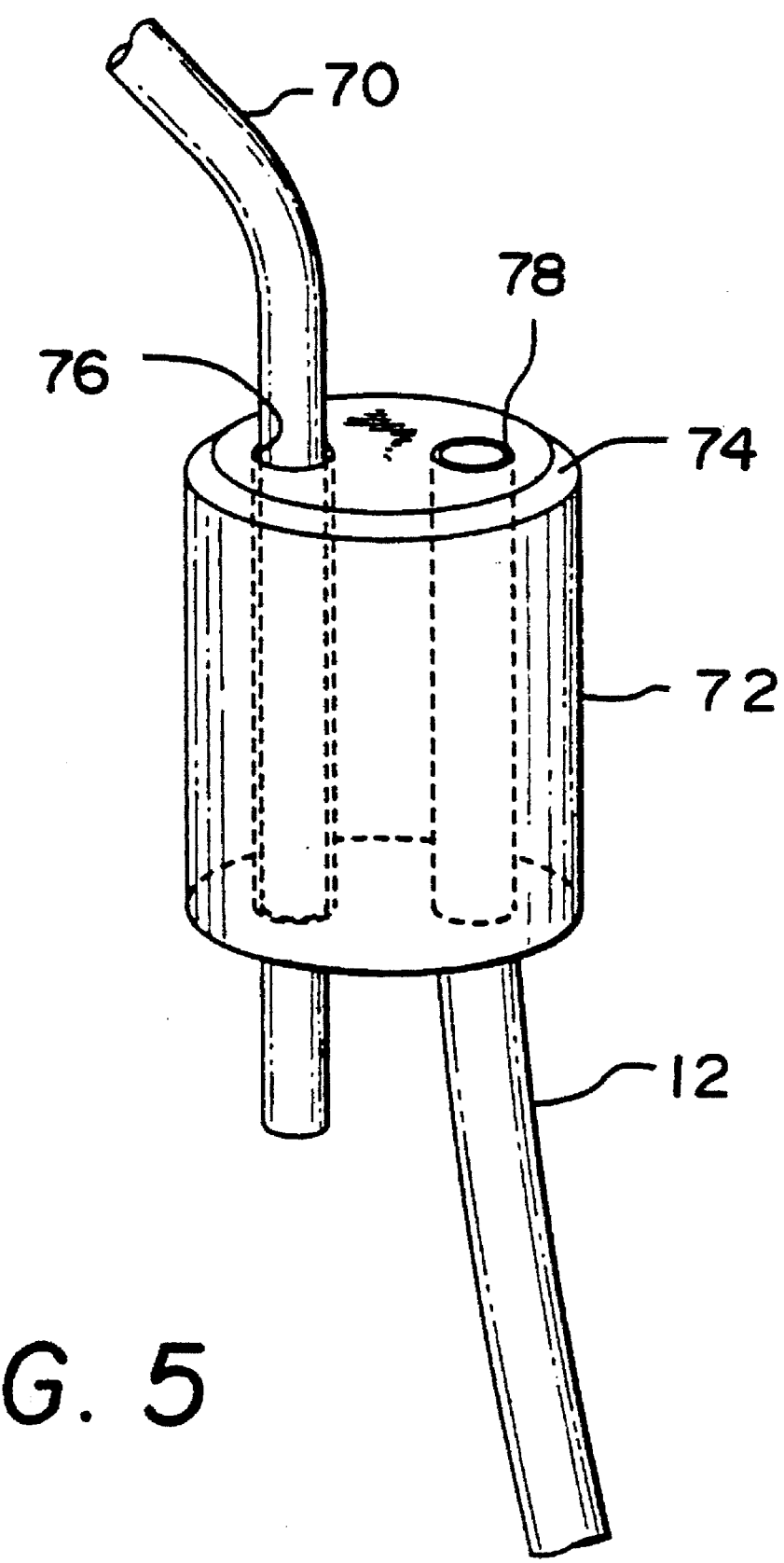
FIG. 5 is a perspective view of a guidewire and sleeve used to control movement of a waveguide.

In order to provide better control of an optical fiber during laser angioplasty, a guidance system may be employed. Referring now to FIG. 5, the guidance system includes a guidewire 70 and a sleeve 72.

The sleeve 72 is preferably between 1 and 200 centimeters in length, and has a rounded tip 74 at its distal end. The tip 74 can be made of stainless steel and glued or welded to the sleeve, or it can be formed integrally on the sleeve 72. The diameter of the tip can vary from 1.2 to 2.5 mm, depending upon the size of the blood vessel. The rounded tip 74 serves as both a dilator to enlarge the blood vessel and as a device to blunt the tip of the optical fiber 12 so as to minimize trauma to the blood vessel.

The sleeve 72 has at least two lumens 76, 78 therein. A first lumen 76 is designed to accept the guidewire 70 and is preferably within the range of twelve-thousandths (0.012) to thirty-eight thousandths (0.038) of an inch in diameter. The diameter of the first lumen may vary, depending on the diameter of the guidewire 70.

The second sleeve lumen 78 is designed to enclose the optical fiber 12, or an array of fibers, if such is the case. The diameter of the second lumen 78 may also vary according to the diameter of the optical fiber 12 or fibers being used. The distal end of the optical fiber 12 is bonded within the second lumen 78 by any suitable means well known to those skilled in the art of bonding.

To use the guidance system, the guidewire 70 is threaded through the lumen of the blood vessel by means of an introducer catheter (not shown). The guidewire 70 is inserted up to the location of a total obstruction in the vessel, or in the case of a subtotal lesion, beyond the lesion.

The sleeve 72 is then mounted onto the guidewire 70, with the guidewire extending through the first lumen 76 of the sleeve. The sleeve 72 and the optical fiber 12, which is bound thereto, are then advanced along the guidewire 70 until the sleeve 72 and the distal tip of the optical fiber 12 are adjacent the lesion to be ablated. The combination of the guidewire 70 and the sleeve 72 ensures that the optical fiber 12 remains in alignment with the blood vessel, thus avoiding perforation of the blood vessel by the tip of the optical fiber 12 during positioning of the fiber or by the laser beam during ablation.

Alternatively, the guidewire 70 may initially be threaded through the first lumen 76 of the sleeve 72, prior to the insertion of the guidewire 70 into the blood vessel. Once the fiber 12 is adjacent the lesion, ablation of the lesion is conducted as described above.

In a preferred embodiment, the second lumen 78 is eccentrically located within the sleeve 72. In such an arrangement, rotation of the optical fiber 12 while it is in the blood vessel causes rotation of the sleeve 72 which causes the radial position of the optical fiber 12 to shift within the blood vessel. Accordingly, rotating the optical fiber 12 during lasing causes a larger lumen to be ablated within the blood vessel.

Once the lasing is completed, the sleeve 72 and the optical fiber 12 can be withdrawn, leaving the guidewire 70 in place within the blood vessel. Angiographic dye can then be injected through a guiding catheter around the guidewire 70 to evaluate the results of the lasing operation. If the results are unsatisfactory, the entire procedure can be repeated, possibly using different laser parameters or fibers.

A further, preferred embodiment of a catheter for coronary laser angioplasty, which operates in accordance with the foregoing principles, is illustrated in FIGS. 6–8. The catheter 80 is multi-compartmented. It includes a center lumen 82 which accommodates a guidewire 84. The guidewire is introduced through a suitable coupling device 86 at the proximal end of the catheter. The center lumen 82 is surrounded by a plurality of circumferentially disposed outer lumens 88. These lumens 88 each house one or more substantially pure synthetic silica fibers 90. In the illustrated embodiment there are three outer lumens 88 each housing two fibers 90. It will be appreciated that a different number of lumens and/or fibers per lumen can be employed, as determined by the relative sizes of the fibers 90, the guidewire 84 and the diameter of the catheter. Furthermore, the guidewire lumen may be eccentrically arranged within the catheter.

An enlarged cross-sectional side view of the distal end of the catheter is shown in FIG. 8. Here, each laser-energy conducting fiber 90 is fused at its end face 91 to a short section of a larger diameter fiber 92. For example, the fibers 90 might have a diameter of 200 microns throughout the length of the catheter 80, and the short end fibers 92 might have a diameter of 300 microns, or a 100 micron diameter fiber may have a short 200 micron diameter fiber fused to its end. Each end fiber 92 can be about 3 mm long, and can be made from the same silica material as the fibers 90. By virtue of the larger diameter fiber at the distal end, the laser beam can expand as it emerges from the fiber, thereby providing a larger area of coverage and subsequently a larger ablation area. Furthermore, the plural fibers located symmetrically around the guidewire provide uniform energy distribution over a larger area.

The fibers 92 are held in place at the end of the catheter by means of a suitable epoxy 94. A gold marker ring 96 can be provided around the catheter at the distal end, to assist in locating the end of the fiber during a fluoroscopy and angiography procedure.

Except at the very end of the catheter where the epoxy 94 is present, there is free space within each outer lumen 88 between the fiber 90 and the walls of the lumen. See also FIG. 22 for an illustration of the free space. If desired, this free space can be used to provide a saline solution, or other contrast media, to the site of the obstruction. The solution can be injected into the catheter through a suitable port 98 at the proximal end, and emerge through holes 100 in the side wall of the catheter at its distal end (see FIG. 8).

In certain situations, there is a need to ablate a large area of a partially or fully occluded vessel in order to maintain an open lumen. The clinical efficacy of ablation in the large peripheral vessels is enhanced when the lumen created is larger than 2 mm. Long term reocclusion of large vessels with low pressure blood flow is reduced When the energy delivery system is used to ablate a hole without subsequent dilation of the vessel.

Laser angioplasty systems for the treatment of nontotal occlusions include systems that have a bundle of fibers placed concentrically around a guidewire lumen, and which are covered in a protective sheath. Small diameter catheters, e.g., 1.0 to 1.7 mm O.D., have a ring of active optical fibers that extends from the center guidewire lumen to the outer protective sheath. Any occlusive material confronted by the advancing catheter will be removed by the active fiber ring.

Traditional guidewire catheter systems are guided through the vessels with a nondeflectable guidewire. However, because plaque is frequently built up eccentrically within the vessel, it is frequently desirable during a procedure to change the general direction of the guidewire, and thus the path of the catheter within the vessel. With a nondeflectable guidewire, it is sometimes difficult to change the direction of the guidewire. For this reason, it is advantageous to have a deflectable guidewire, and in particular, a deflectable guidewire that can be manipulated by the operator from the proximal end thereof.

Such a deflectable guidewire 206 is disclosed in FIGS. 9-14. The guidewire 206 includes a core 208 extending substantially the entire length of the guidewire 206. A wire coil 210 is positioned about the core 208 at a position along the guidewire where flexibility or deflectability is desired, preferably at the distal end thereof.

The coil includes three sections, a first section 210A, a middle section 210B, and a third section 210C. The outside diameter of the coil 210 is between 0.012 and 0.038 inches, preferably about 0.018 inches. The first and second sections 210A and 210B are preferably manufactured from a length of radiopaque wire. The first section 210A of the wire coil is preferably about 2–3 cm. in length. At the proximal end of the first section 210A, the wire coil 210 is mechanically fixed to the core 208 at joint 214 through a method such as soldering or brazing.

Figure 9:
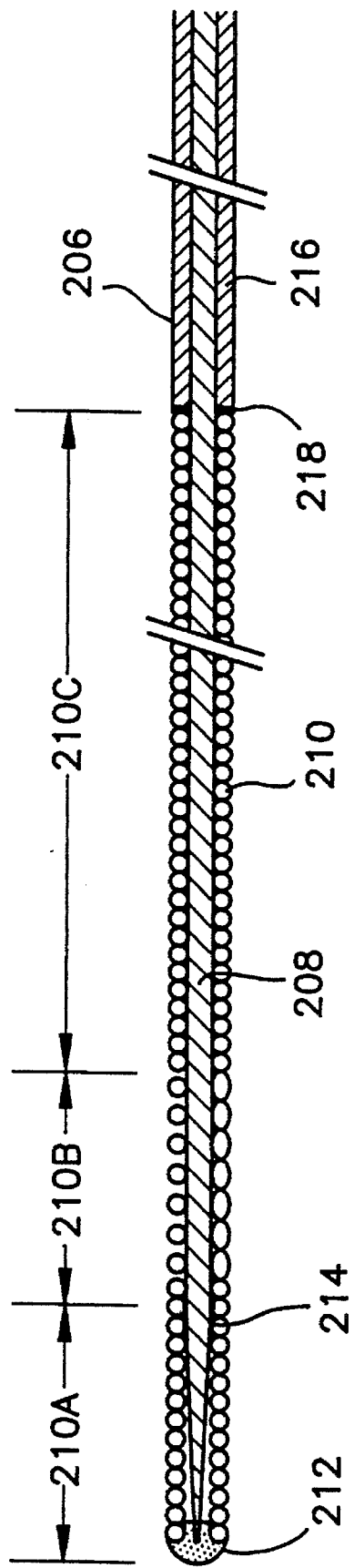
FIG. 9 is a cross-sectional view of a deflecting guidewire according to the present invention.

The wire comprising the middle section 210B of the wire coil is mechanically deformed, or otherwise has a nonuniform cross section. As seen in FIGS. 9 and 10, the wire is deformed or flattened on one side 208A of the core 208 so that when the wire is straight, gaps occur between the individual turns of the wire coil on the opposite side 208B of the core.

Alternatively, as indicated in FIG. 12, the diameter D2 of the wire on one side of the core can be reduced by electropolishing or chemical etching. Or, the diameter D1 of the wire on one side of the core can be built up by selectively depositing material by a plating process.

At the proximal end of the third section 210C, the wire coil 210 is fixed to an intermediate sheath 216 at joint 218 by a method such as soldering or brazing. The intermediate sheath 216 is a noncompressible conduit that retains and protects the core 208 and extends from the wire coil 210 to the proximal end of the guidewire. The intermediate sheathing is preferably semiflexible hypodermic tubing that can be made from any appropriate material.

Figure 13:
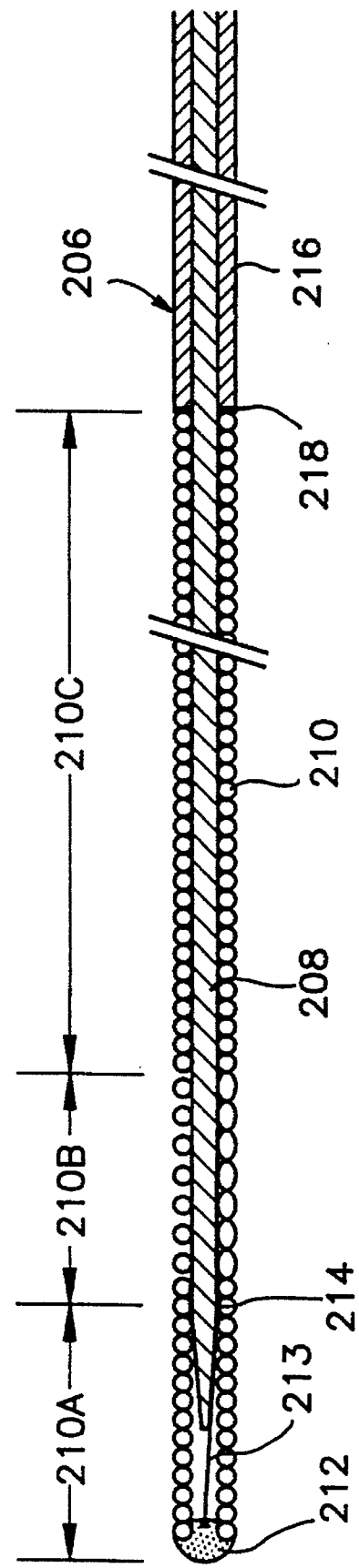
FIG. 13 is an alternative embodiment of the present invention.
Figure 14:
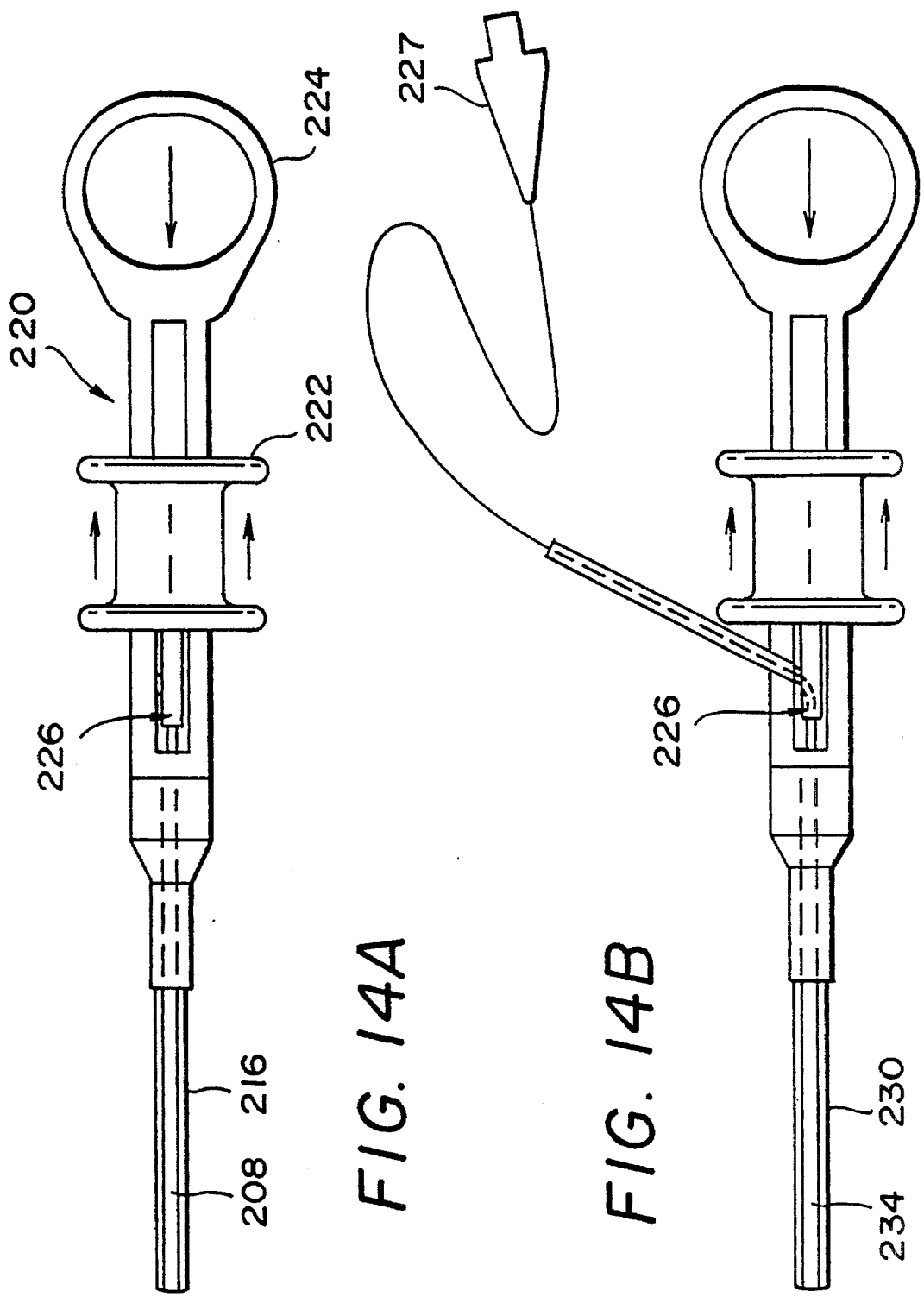
FIG. 14A is a view of a control mechanism for the deflecting guidewire of FIG. 9.
FIG. 14B is a view of a control mechanism for the deflecting catheter of FIG. 15.

At the distal end of the guidewire is a blunt tip 212 for minimizing traumatic injury to the vessel in which it is being used. The distal end of the core 208 may be affixed to the distal blunt tip 212, as illustrated in FIG. 9. Alternatively, as illustrated in FIG. 13, it is not necessary that the core 208 extend all the way to the blunt tip 212. In that case, it is only necessary that the core 208 be fixed to the wire coil 210 at the distal end of the deformed second section of the wire coil 210B. If the core 208 does not extend to the blunt tip 212, it is preferable to have a substitute material 213 extend between the blunt tip 212 and the core 208 in order to prevent the coil 210 from being stretched and/or unwrapped. It may be preferable to use a fine wire or ribbon as the substitute material 213 so as to maintain maximum flexibility in the tip of the catheter.

The core 208 is fabricated from a material having a high tensile strength, preferably from a single piece of stainless steel. The core 208 slides freely within the second and third sections of the coil 210B, 210C and within the intermediate sheath 216. As indicated above, and in FIG. 9, the core 208 is secured to the wire coil 210 at the joint 214 between the first and second sections of the wire coil 210A, 210B. At its proximal end, the core 208 is secured to a deflection handle 220. See FIG. 14A.

The deflection handle 220 is designed to apply tension to the core 208, which in turn causes the second section 210B of the wire to deflect as this is the only area of the outer sheath that has spacing between the coil where a change in length can occur. See FIGS. 11 and 12. The deflection handle 220 includes a finger grip 222, and a thumb ring 224. The core 208 of the guidewire is fastened to a pin 226, which is in turn connected to the finger grip 222. The sheath 216 is fastened to a nonmoving part of the deflection handle 220 so that when the finger grip 222 and the thumb ring 224 are brought together, as shown by the arrows in FIG. 14A, a tension is created in the core 208. Because of the unevenness of the second section 210B of the wire, the wire coil, and thus the entire guidewire deflects at the region of the second section 210B of the guidewire.

By selecting a core material of high torque strength, the entire guidewire can be rotated by rotating the deflection handle, which is attached to the core 208. Such a rotation permits the user to deflect the guidewire in any radial direction.

Figure 15:
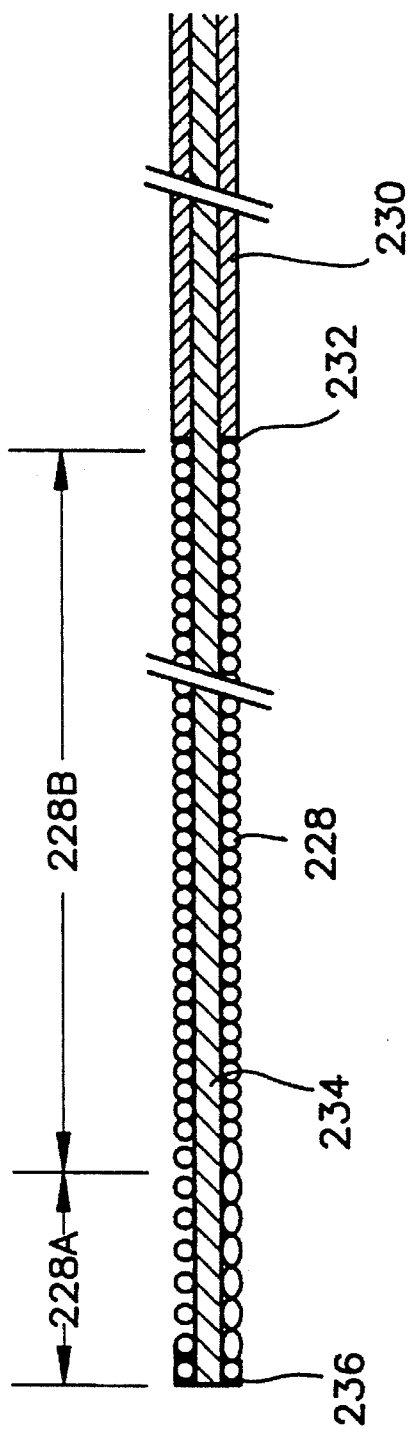
FIG. 15 is a cross-sectional view of a deflectable fiber optic catheter according to the present invention.

The concept of using a nonuniform wire to deflect a guidewire can also be applied to an energy transmitting guidewire or a catheter system. Turning attention to FIG. 15, the wire coil and intermediate sheathing arrangement can be applied to an optical fiber or optical fiber bundle. In the embodiment disclosed in FIG. 15, a wire coil 228 includes a first section 228A and a second section 228B. The first section has a nonuniform cross section like the second section 210B of the FIG. 9 embodiment. The wire comprising the first section 228A of the wire coil is mechanically deformed, or otherwise has a nonuniform cross section. As seen in FIG. 15, the wire is deformed or flattened on one side so as to create gaps between the individual turns of the wire coil on the opposite side. Alternatively, the diameter of the wire on one side of the core can be reduced by electropolishing or chemical etching. Or, the diameter of the wire on one side of the core can be built up by selectively depositing material by a plating process.

An intermediate sheathing 230 is fixed to the proximal end of the wire coil 228 via a joint that is made by a process such as soldering or brazing. A fiber optic core 234 extends from the distal end of the wire coil 228 through the proximal end, and is ultimately connected to a source 227 of laser energy. See FIG. 14B. At its distal end, the fiber optic core 234 is fixed to the distal end of the wire coil 228 by means of epoxy 236 or some other suitable method. The distal end of the fiber optic core 234 is of course exposed so that laser energy may be transmitted forwardly from the catheter.

At the proximal end of the intermediate sheathing and fiber optic core 234, a deflection handle is mounted. See FIG. 14B. The deflection handle is substantially identical to the deflection handle illustrated in FIG. 14A. Accordingly, a detailed description thereof will not be repeated herein. By appropriate control of the deflection handle, the wire coil, and thus the fiber optic core 234, can be deflected and thus guided within a vessel.

Figure 16:
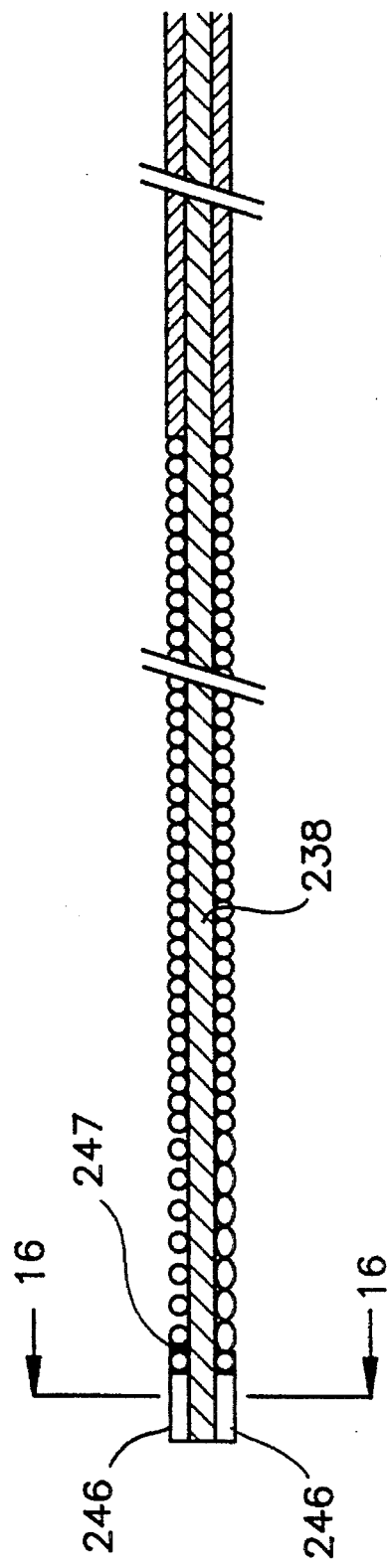
FIG. 16 is a cross-sectional view of a deflectable fiber optic catheter having ultrasound sensors mounted at the distal end thereof.
Figure 17:
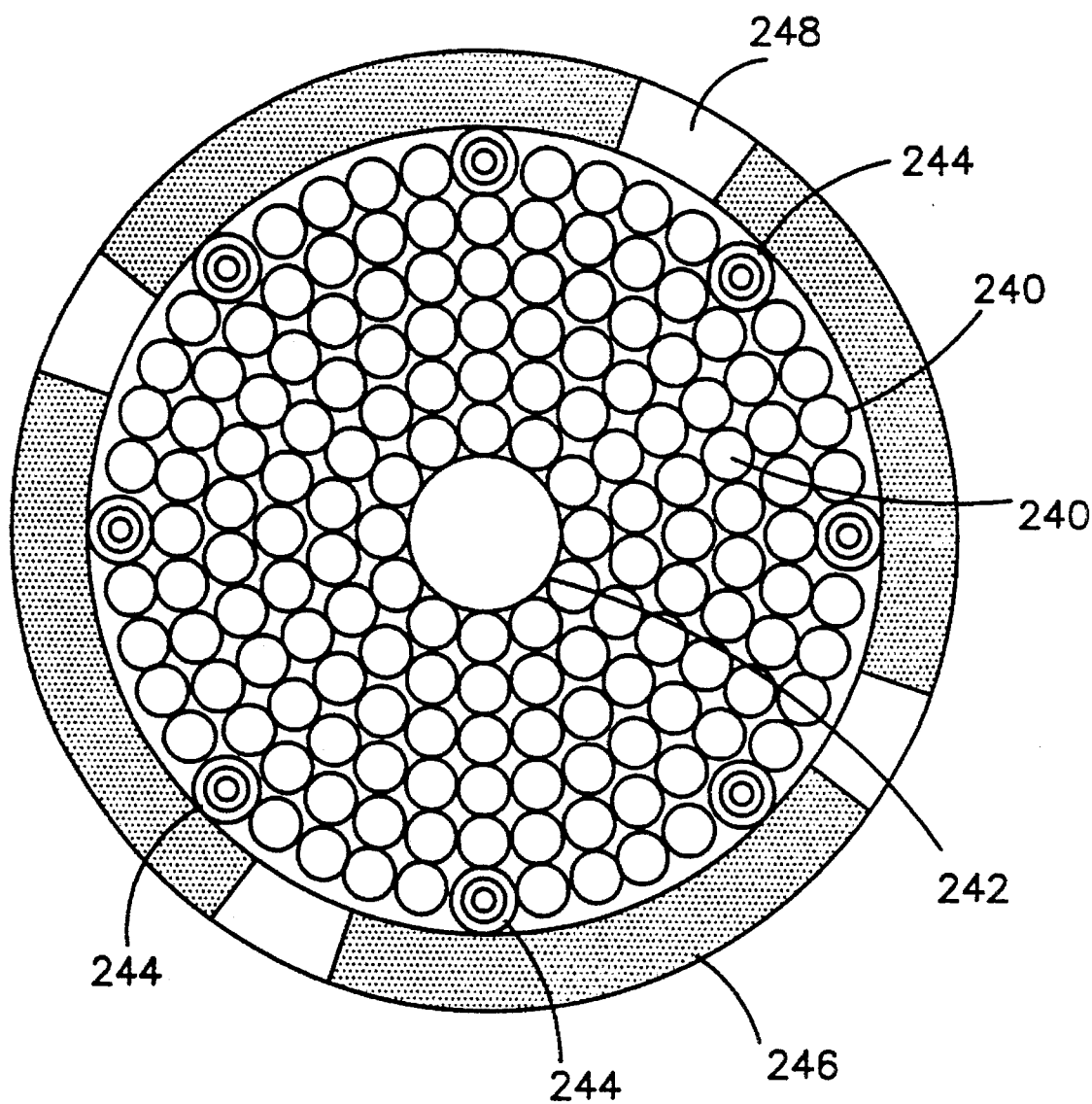
FIG. 17 is a cross-sectional view of the catheter of FIG. 16.
Figure 18:
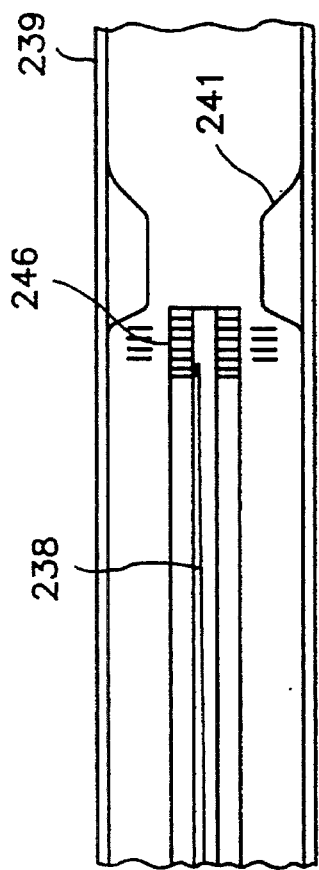
FIG. 18 is a cross-sectional view of an occluded vessel in which a catheter employing an ultrasound system is disposed.

FIGS. 16–18 disclose a catheter system substantially identical to the system disclosed in FIG. 15, except that the system disclosed in FIGS. 16–18 includes an ultrasound system for facilitating guidance of the catheter during an ablating procedure. The core 238 comprises a plurality of small stranded optical fibers 240, a central optical fiber 242, and wires 244 for transmitting signals to and from ultrasound sensors at the distal end of the catheter. The small optical fibers 240 are approximately 50 to 100 microns in diameter and the large central optical fiber 242 is approximately 150–200 microns in diameter. The actual sizes of the wires may vary in different applications. Alternatively, the central optical fiber 242 could be the same diameter as the outer fibers. In one embodiment, the central optical fiber 242 is 100 microns and the surrounding fibers 240 are 80 microns. The outside diameter of the catheter is preferably between 1.0 mm to 2.0 mm.

At the distal end of the catheter, four ultrasound sensors 246 are symmetrically arranged about the optical fibers. The ultrasound sensors are fixed in place with epoxy 248, which also is used to fill in the gaps between each sensor 246. The ultrasound sensors comprise thin film ultrasound emitter/ detectors, and are arranged so as to emit and detect signals in a radial direction with respect to the catheter. The ultrasound sensors are of the same type used in high-resolution, intraluminal imaging. However, in the present case, only a low pixel, low resolution system is used to merely delineate the blood vessel wall 239 without showing in great detail the diseased, or occluded, section 241 inside the vessel.

Each of the ultrasound sensors 246 looks in a radial direction with respect to the catheter and sends a signal to the operator that is representative of the distance between the sensor and the wall of the vessel. In this manner, the operator can easily determine when the catheter is too close to the wall. The purpose of the ultrasound sensors is to detect the location of the wall so that during the ablating procedure, the laser-carrying optical fibers do not inadvertently contact the vessel wall.

Figure 19B:
FIGS. 19A and 19B are images from a catheter employing an ultrasound system within a vessel.
Figure 19A:

Because the ultrasound system is a low resolution system, the image seen by the operator is an outer circle representing the vessel wall and an inner circle representing the catheter. See FIGS. 19A and 19B. FIG. 19A illustrates the image seen when the catheter is in the center of a vessel. FIG. 19B illustrates the image seen when the catheter is adjacent a vessel wall.

The catheter may have a marker band 247 fixed to the distal end of the catheter. The marker band 247 is preferably made from a radiopaque material, such as gold, so that it can be detected by an external x-ray, or comparable detecting system, in order to facilitate the guiding of the catheter to the lesion in the vessel. Thus, the catheter is first guided to the lesion using the external detecting system and the radiopaque marker. Then, control during the ablating process can be had with the use of the ultrasound system described above. Instead of using a radiopaque marker band, the deflectable coil itself may be made from a radiopaque material.

The deflectability of the catheter facilitates the guiding of the catheter to the lesion to be ablated. However, during the ablating process, the tip of the catheter can be selectively deflected to permit a hole to be ablated that is larger in diameter than the diameter of the catheter.

Figure 20:
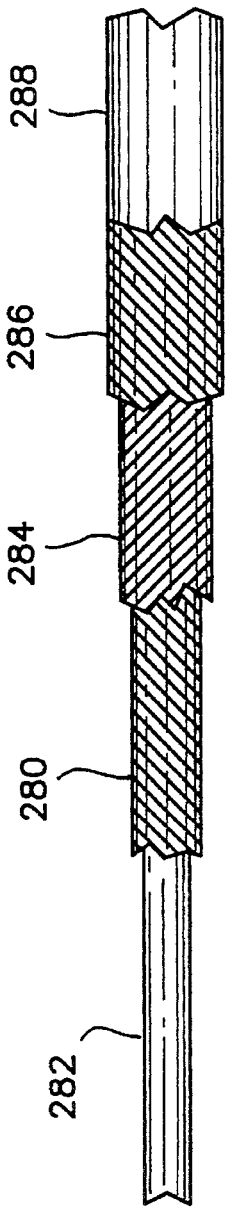
FIG. 20 is a view of catheter in which optical fibers are stranded in alternating layers.

To increase the strength and torque of the core 238 of the catheter, each row of optical fibers may be stranded, i.e., wound or twisted, in a direction that is opposite to the direction in which each adjacent row is wound. Although the catheter in FIGS. 16–18 includes a solid fiber optic core 238, the concept of stranding the fibers in opposite directions can also be applied to a catheter that has a center guidewire lumen. FIG. 20 illustrates a cutaway view of a catheter similar to the catheter of FIGS. 16–18, except that it has a center guidewire lumen 282. There are shown only three layers of optical fibers stranded in accordance with the present invention. A preferred embodiment may have five or six layers. A first layer 280 of optical fibers is wound in a first (e.g., counterclockwise) direction about the plastic center guide lumen 282. A second layer 284 of optical fibers is wound over the first layer in an opposite direction, and a third layer 286 of optical fibers is wound over the second layer in the same direction as the first layer 280. A plastic outer cover 288 covers the third layer 286.

Figure 21:
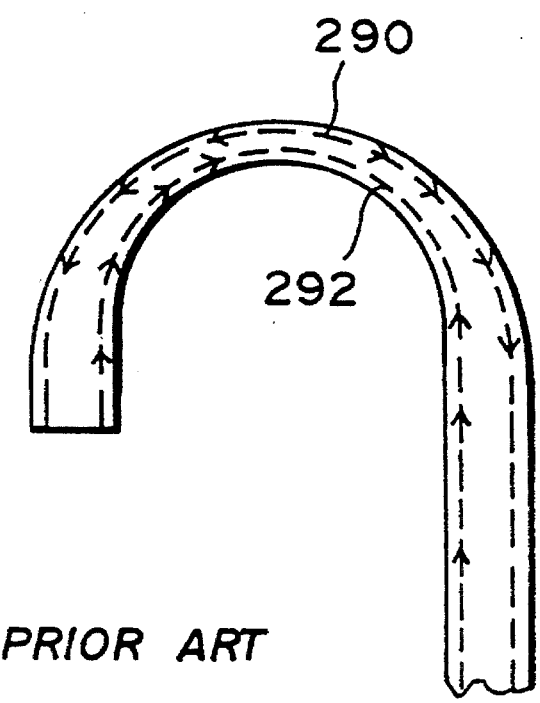
FIG. 21 is an illustration of a prior art catheter in a bent position.
Figure 22:
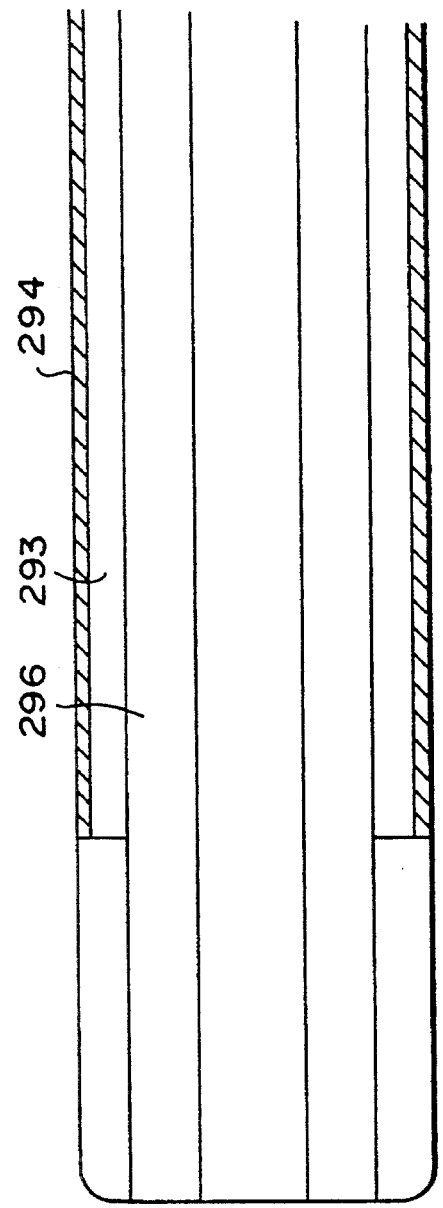
FIG. 22 is a cross-sectional view of a catheter in which optical fibers are arranged in a parallel manner.

As illustrated in FIGS. 21 through 24, the alternatingly stranded fibers perform better than coaxial parallel fibers. FIG. 21 is a simplified illustration of a catheter bent in 180°, and which has coaxial parallel fibers. A single exemplary fiber 290 is shown on the outer side of the bend, and a single exemplary fiber 292 is shown on the inner side of the bend. The outer fiber 290 tends to be stretched in tension, while the inner fiber 292 tends to be compressed. Both fibers are urged toward the center of the catheter as illustrated in FIG. 21. To accommodate these uneven forces acting on the fibers, such coaxial fiber catheters are generally designed, as illustrated in FIG. 22, with some clearance 293 between the covering tube 294 and the fibers 296. The clearance is not an effective use of catheter space.

Figure 23:
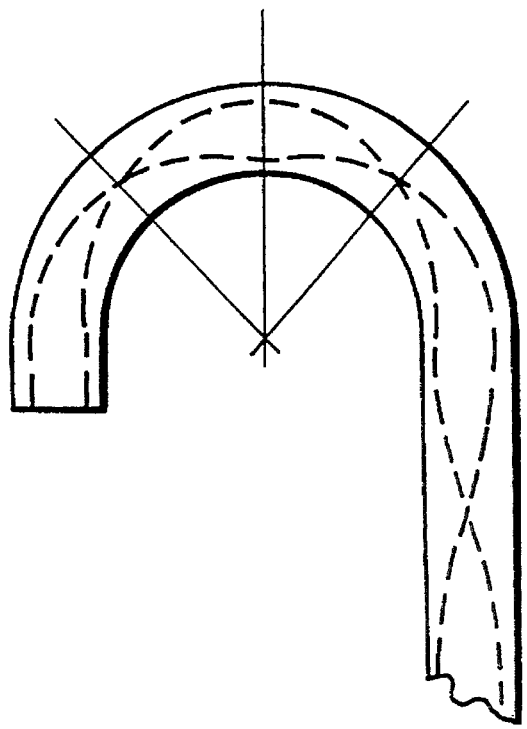
FIG. 23 is an illustration of a catheter according to the present invention in a bent position.
Figure 24:
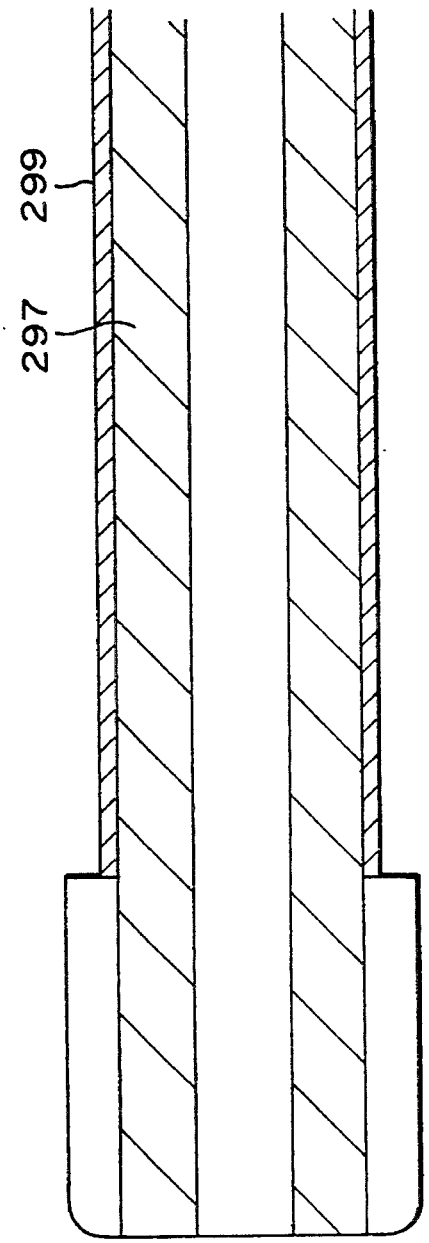
FIG. 24 is a cross-sectional view of a catheter in which the optical fibers are stranded.

In contrast to the design illustrated in FIGS. 21–22, a simplified illustration of fiber optics alternatingly stranded in accordance with the present invention is shown in FIGS. 23–24. As can be seen in FIG. 23, in a stranded catheter, the tensile and compressive forces caused by bending the catheter are evenly distributed among the fibers. As a result, there is little or no tendency for the catheter to flatten, as is illustrated in FIG. 21. In addition, as is illustrated in FIG. 24, there is no need to provide for clearance between the fibers 297 and the outer cover 299 if the fibers are stranded in accordance with the present invention. As a result, the overall diameter of the catheter can be made smaller. Another advantage of the stranded arrangement is that the catheter can be twisted more easily in that the stranded catheters will more easily transmit torque than the coaxial fibers. For example, if the assembly of FIG. 20 is twisted clockwise, the third layer 286 will tend to reduce in diameter and increase in length, while the second layer 284 will have the opposite effect, tending to increase in diameter and decrease in length. If the assembly is twisted counterclockwise, the second layer 284 will tend to reduce in diameter and increase in length while the first layer 280 will tend to increase in diameter and decrease in length.

Although FIG. 20 illustrates fibers wrapped in alternating directions, alternatively the fibers may be otherwise arranged within the catheter so that when the catheter is bent, the bending stresses are absorbed by the fibers in a substantially uniform manner. This is accomplished by arranging the fibers such that each fiber is bent a substantially equal amount during bending of the catheter.

When performing angioplasty operations in large diameter vessels it is preferable to use catheters of a large diameter which have a large effective ablating area. In traditional large diameter catheters having a central guidewire lumen, there is a large number of optical fibers in the lumen between the outer sheath and the central guidewire lumen. Such a large number of fibers reduces the flexibility of the catheter.

The outer diameter of the effective ablating area of the catheter can be increased, without decreasing the flexibility of the catheter, by increasing the outer diameter of both the outer sheath and the central guidewire lumen at the distal end of the catheter. The increased size of the outer sheath and guidewire lumen increases the diameter of the ring of active fiber optics, without requiring additional fibers. Thus, the flexibility of the catheter is not decreased. By increasing the diameter of the central guidewire lumen only at the distal end of the catheter, the likelihood of ischemia is decreased.

Figure 25:
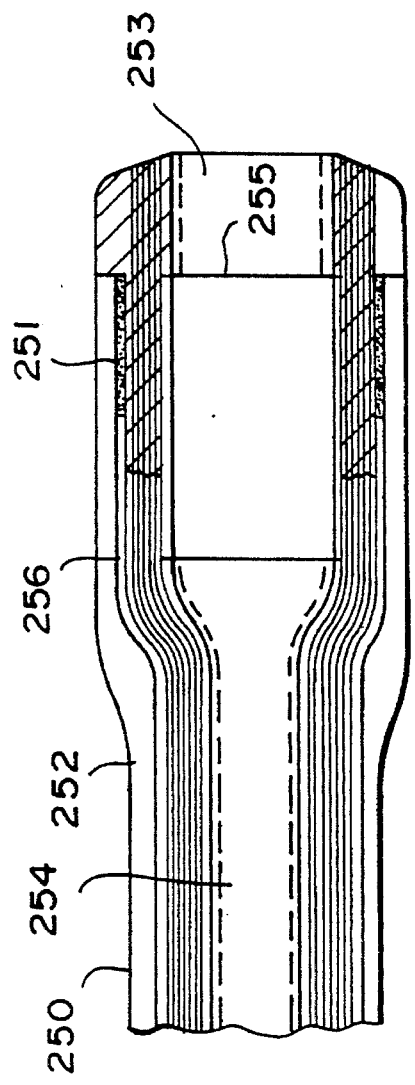
FIG. 25 is a cross-sectional view of a catheter having an expanded tip so as to accommodate a specially designed guidewire.
Figure 26:
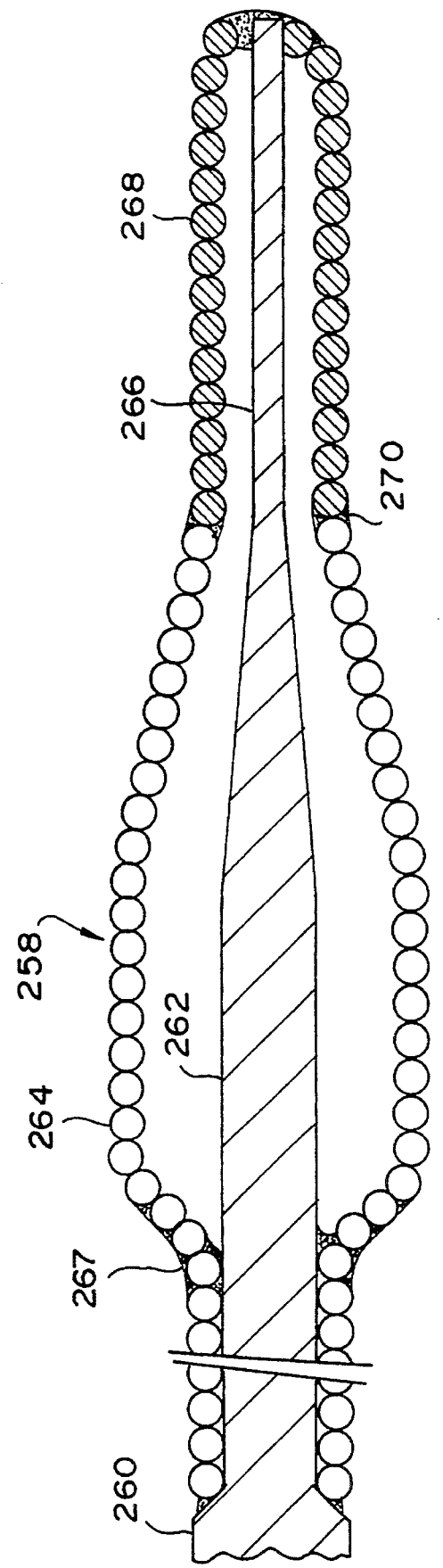
FIG. 26 is a side view of the tip of a "carrotwire" guidewire.

In FIGS. 25 and 26, such a catheter system is disclosed. Referring to FIG. 25, a catheter 250 has an enlarged diameter at its distal end. The outer sheath 252 has an increased diameter at the distal end thereof. At the center of the catheter 250 is a guidewire lumen 254, which has a similarly enlarged diameter at its distal end. Between the guidewire lumen 254 and the outer sheath are one or more lumens 256 for optical fiber.

Within lumen 256 is a radiopaque marker band 251 for facilitating guiding the catheter through a body lumen. The marker 251, which may be made from gold, is detectable by an external system, such as an x-ray system. A polyurethane bushing 255 is placed within the guidewire lumen 254 to support the enlarged expanded portion 253 of the catheter.

In a preferred embodiment, the internal diameter of the expanded portion 253 of the guidewire lumen is approximately 0.041 inches. The expanded portion of the optical fiber lumen is ring shaped, and has an outer diameter of approximately 0.085 inches and an inner diameter of approximately 0.056 inches. About 360 50µ fibers are enclosed within the lumen 256. The overall outer diameter of the expanded portion of the catheter is approximately 0.095 inches. As illustrated in FIG. 25, the front face of the catheter may be angled 25° from a plane normal to the axial direction of the catheter.

The guidewire 258 disclosed in FIG. 26 is designed for use with the catheter of FIG. 25, and is referred to as a "carrotwire" guidewire. The main portion of the guidewire comprises a length of stainless steel shaft 260, preferably about 0.018" in diameter, that extends from the proximal end of the guidewire. Fixed to the distal tip of the shaft 260 is a secondary shaft 262 of reduced diameter, e.g., 0.008", and having a length of about 19 cm. The diameter of the last four centimeters of the secondary shaft 262 is further tapered to a diameter of about 0.002". At the distal tip of the secondary shaft 262 is a flat strip 266 of stainless steel having a width of about 0.002".

The secondary shaft 262 is wrapped with a stainless steel wire coil 264. The first 13 cm. of the wire coil 264 adjacent the main stainless steel shaft is wrapped in substantial contact with the secondary shaft 262 so that the overall diameter of the coil is about 0.018", i.e., about the same diameter as the main stainless steel shaft. At the distal end of the 13 cm. length, the diameter of the coil is expanded to approximately 0.039". At this point of expansion, a radiopaque (e.g., gold) solder marker 267 is fixed to the coil so that the distal end of the guidewire 258 can be easily detected by an external x-ray system. The expanded portion of the wire coil extends for about 2 cm., at which point the diameter of the coil is gradually reduced to about 0.018" at the point where the secondary shaft is fixed to the strip 266 of stainless steel. At the distal tip of the guidewire, a platinum coil of wire 268, which covers the strip 266 of stainless steel 266 is affixed to the stainless steel coil of wire 264 with a soldered joint 270. The distal tip of the platinum coil of wire 268 is soldered to the tip of the stainless steel strip 266. The tip of the guidewire is blunt so as to minimize traumatic injury to the vessel in which it is being used. Note that the expanded portion of the wire coil 264 is adapted to fit within the expanded portion of the center guidewire lumen 254 of FIG. 25.

Because both the catheter 250 and the guidewire 258 are expanded at their distal end, the catheter 250 and the guidewire 258 coact so as to center the distal tip of the catheter 250 within the vessel, to keep the distal tip of the catheter 250 collinear to the axis of the host vessel, and to mechanically displace occlusive material in an outward radial direction such that the occlusive material will be presented to the active fiber ring of the catheter 250.

Figure 27:
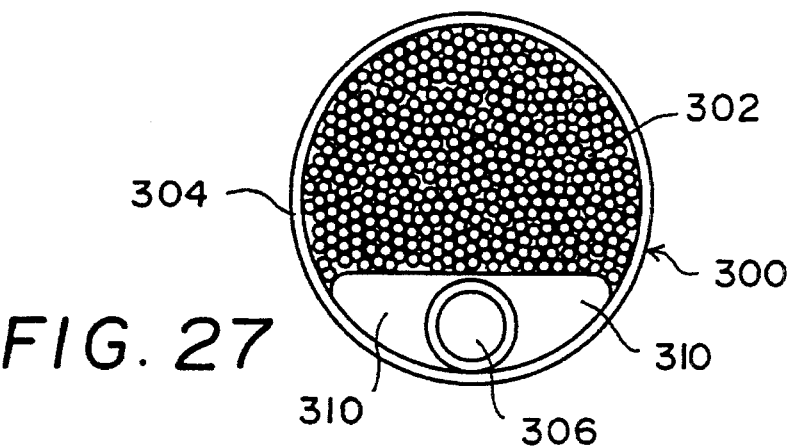
FIG. 27 is a cross-sectional view of an eccentric guidewire catheter according to the present invention.
Figure 28:
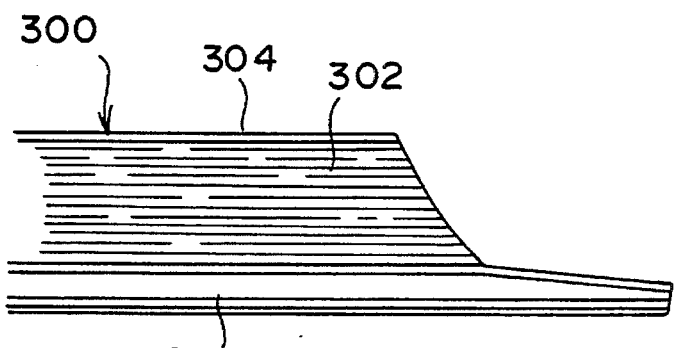
FIG. 28 and 29 are side views of the catheter of FIG. 27.
Figure 29:
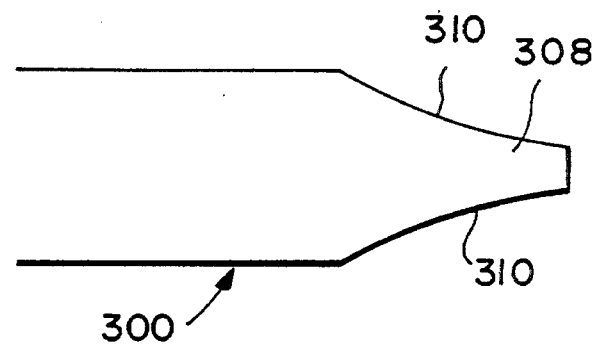

Turning attention to FIGS. 27–29, an over-the-wire catheter 300 having an eccentric body of optical fibers 302 is disclosed. The catheter 302 includes an outer sheath 304 that encloses the plurality of optical fibers 302 and a guidewire lumen 306 that forms a fountain pen-like point 308 at the distal end thereof. The point 308 has tapered walls 310 that form a gradual transition from the tip to the outer sheath 304 of the catheter. The point 308 may be made integral with the outer sheath 304.

Figure 30:
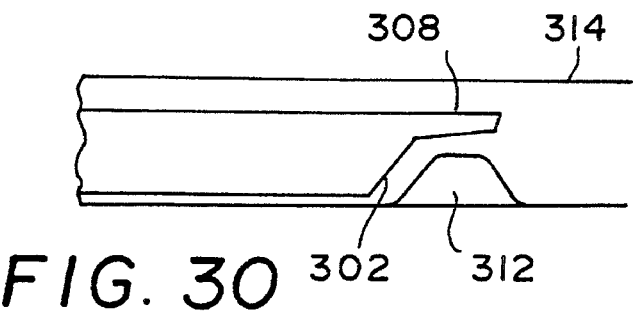
FIG. 30 is a view of the catheter of FIG. 27 in an occluded vessel.

As illustrated in FIG. 28, the optical fibers 302 themselves are of an unequal length, with the fibers closest to the guidewire 306 being longer than those farther away from the guidewire. The varying length of the optical fibers is optimal for situations where a lesion 312 is located on one portion of the vessel 314. As seen in FIG. 30, the guidewire lumen can pass over the lesion 312 and the graduated length of the optical fibers 302 tends to conform to the shape of the lesion.

The following systems address the problems of making large diameter holes in blood vessels using a small overall diameter delivery system. Turning attention now to FIG. 31, a blood vessel 114 is shown with a lesion 116 therein. A catheter 118 includes a plurality of optical fibers 120 evenly distributed about a concentrically mounted inflatable balloon 122. The optical fibers 120 may be 50–400 microns. A guidewire 124, larger than 0.012 inches in diameter, is concentrically located in a center lumen within the balloon 122. If desired, a metallic (gold) marker 126 may be located adjacent the distal end of the catheter, such that the catheter 118 may be located by an x-ray or fluoroscopy system.

In operation, the guidewire 124 is inserted through the lumen or blood vessel 114 until the guidewire passes through the lesion 116 that is to be ablated. The catheter 118 is then conveyed along the guidewire 124 until the distal end of the catheter 118 contacts the lesion 116. The fibers 120 deliver an initial dose of high energy laser pulses to ablate the inner portion of the lesion 116. Subsequently, the balloon 122 is inflated to a predetermined pressure which then forces the fibers 120 into an array of a larger diameter. A subsequent delivery of high energy pulsed laser is then delivered to ablate the outer peripheral portions of the lesion 116. The balloon 122 may be additionally inflated if necessary to obtain an array of fibers 120 of a still larger diameter.

With reference to FIG. 32, an additional preferred embodiment of the present invention is disclosed. A catheter 128 has three balloons 130 located in an equally spaced arrangement at the distal end of the catheter 128. A first lumen 132 is positioned concentrically among the balloons 130. In the first lumen 132 is disposed a fiber optic instrument 133. If desired, a guidewire may be retained in a second lumen adjacent the first lumen 132. Additional lumens may also be included at the center of the balloons 130 to accommodate other instruments to assist with illumination or flushing, for example.

In operation, the lumens at the center of the catheter may be positioned or tilted by selectively inflating and deflating the three balloons 130. In one mode of operation, the balloons may be inflated sequentially and continuously so as to selectively revolve the fibers in a circular pattern along the perimeter of the catheter. The fibers may be centered by inflating all of the balloons.

In another embodiment, two, four or any other number of balloons may be used instead of three.

As in the embodiment shown in FIG. 31, the embodiment shown in FIG. 32 may also include a marker, such as a gold band, at the distal end of the catheter.

Figure 33:
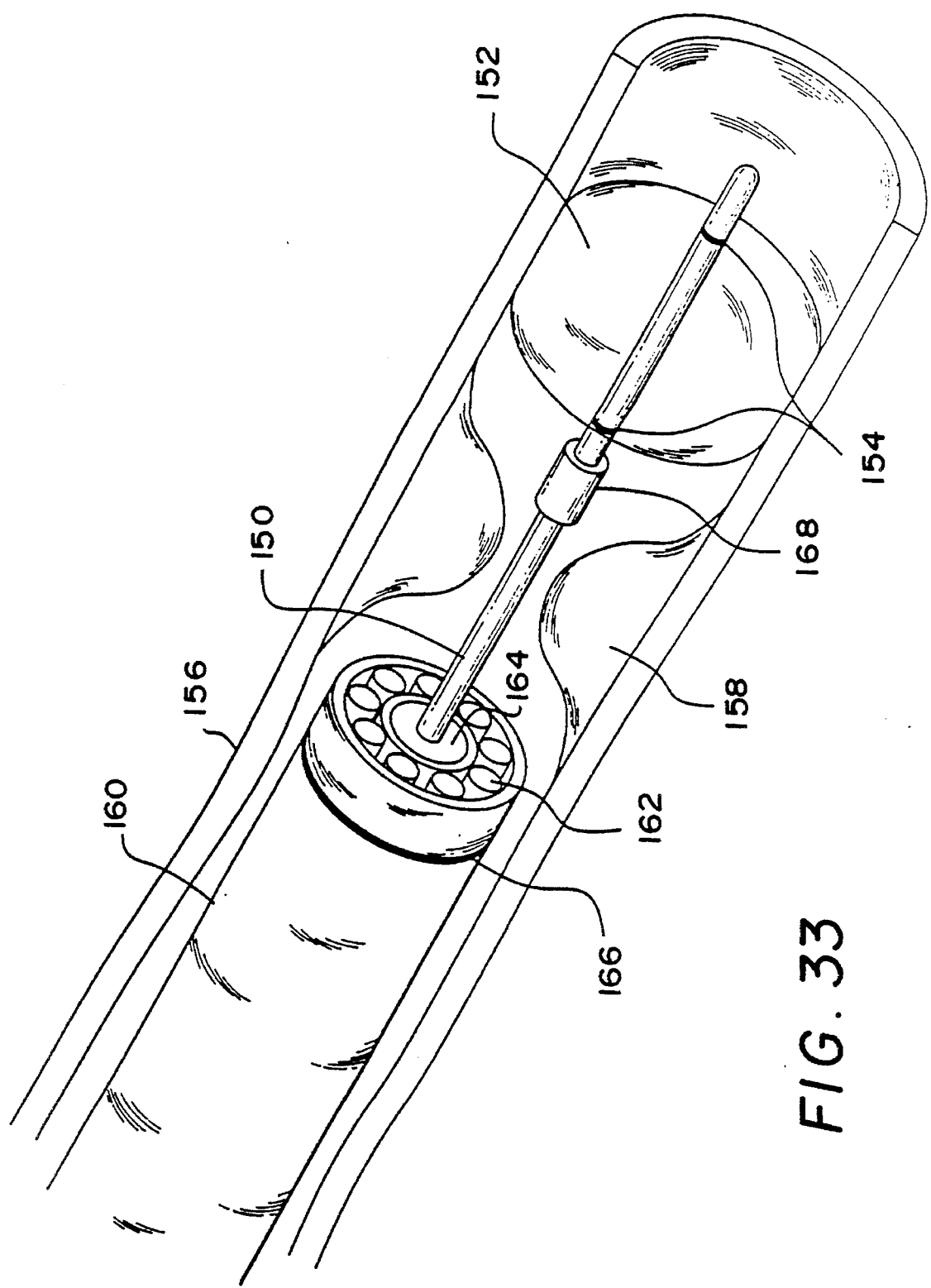
FIG. 33 is a perspective view of an alternative embodiment of a multilumen catheter.

Another preferred embodiment of the present invention is illustrated in FIG. 33. In this embodiment a guidewire 150 has a balloon 152 at the end thereof. Markers 154 are mounted on the guidewire 150 adjacent the balloon 152. The guidewire 150 is disposed through a guidewire lumen 164 in the center of a catheter 160. The catheter 160 further includes a plurality of fibers 162 arranged in an annular pattern about the guidewire lumen 164. If desired, a marker 166, such as a gold band, can be placed around the distal end of the catheter 160 to facilitate detection of the catheter.

In operation, the guidewire 150 with the balloon 152 at one end thereof is inserted through the blood vessel until it is located beyond the lesion 158. The balloon 152 is then inflated, thus centering the guidewire 150 within the vessel. Such centering of the guidewire 150 minimizes the likelihood that the catheter 160 will contact the walls of the blood vessel 156 during the ablation process. A stop 168 may be placed on the guidewire 150 so as to prevent the catheter 160 from contacting and thus possibly rupturing the balloon 152.

The fibers 162 in the catheter preferably range from about 50 to 300 microns. The guidewire lumen 164 is large enough to allow free movement over a standard guidewire ranging from 0.014 to 0.038 inches in diameter.

Figure 34:
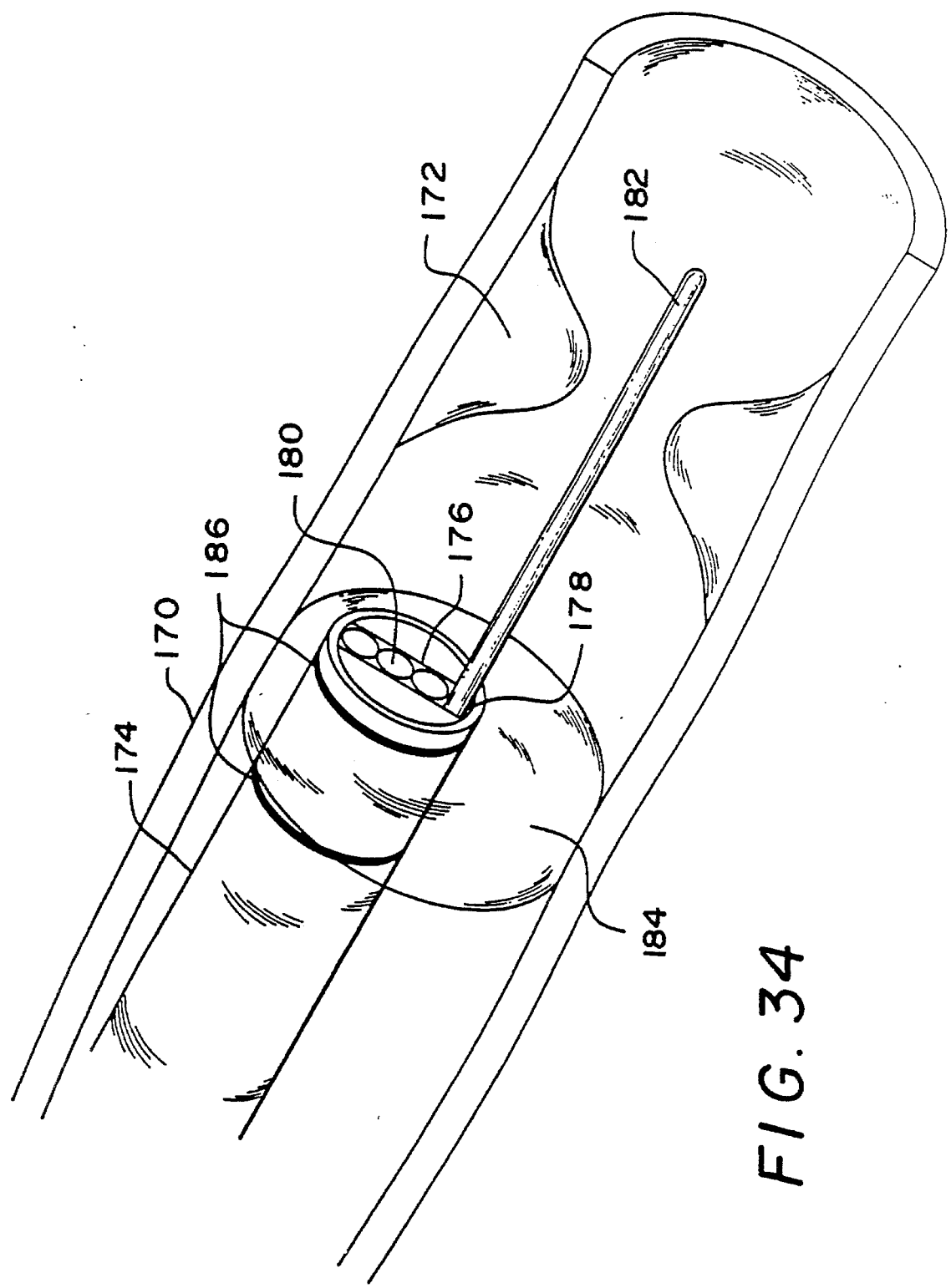
FIG. 34 is a perspective view of another alternative embodiment of a multilumen catheter.

With reference to FIG. 34, another preferred embodiment of the present invention is disclosed within a blood vessel 170 having a lesion 172 therein. A catheter 174 includes a guidewire and flushing lumen 178 located adjacent an inner edge of the catheter. An optical fiber lumen 176 has a width that extends from the guidewire and flushing lumen 178, through the center of the catheter to the edge of the catheter diametrically opposite the guidewire and flushing lumen 178. A plurality of optical fibers 180 made of substantially pure silica are disposed within the optical fiber lumen 176, and a guidewire 182 is disposed within the guidewire and flushing lumen 178. A balloon 184 is bonded at one point to the outer surface of the catheter 174.

To operate, an initial ablation is performed with the balloon 184 in an uninflated condition. The ablation is effected by delivering a high energy pulsed laser, such as from an Excimer laser, through the optical fibers 180 while advancing and rotating the fibers about the guidewire 182. The rotation enables the fibers to ablate a circular area about the size of the catheter outer diameter.

In the next stage, the outer balloon is inflated, thus urging the fibers into a larger diameter. A second ablation is performed with the balloon inflated and while advancing and rotating the catheter so as to ablate an annular area having a diameter larger than the diameter of the circular area ablated during the first stage. During the second stage, the balloon is inflated to a predetermined size in order to ensure that the second annular area is contiguous to the circle ablated during the first stage.

The Excimer energy is only capable of ablating a lesion in a forward direction and does not require that the blood between the lesion and the optical fibers be displaced with a solution, such as saline, that is transparent to the laser. In addition, the laser transmitted through the optical fibers is capable of ablating a lesion in a blood field. Therefore, there is no necessity to block the blood flow around the catheter during the ablation process.

The tip of the catheter should have a round, conical, distal tip to minimize the trauma to the vessel wall. The optical fibers 180 comprise a highly flexible array of fibers that may range in size from 50 to 400 microns in diameter, with a possible enlarged fiber tip output diameter to create a large ablation area. The fibers which are immobilized at the distal end of the catheter by epoxy are polished to form the round distal tip.

The guidewire used to advance the catheter over is commonly used in interventional radiology and cardiology and is preferably larger than 0.012 inch.

If desired, markers 186, such as gold bands can be placed at the distal of the catheter to facilitate monitoring of the catheter by x-ray or fluoroscopy.

Figure 35:
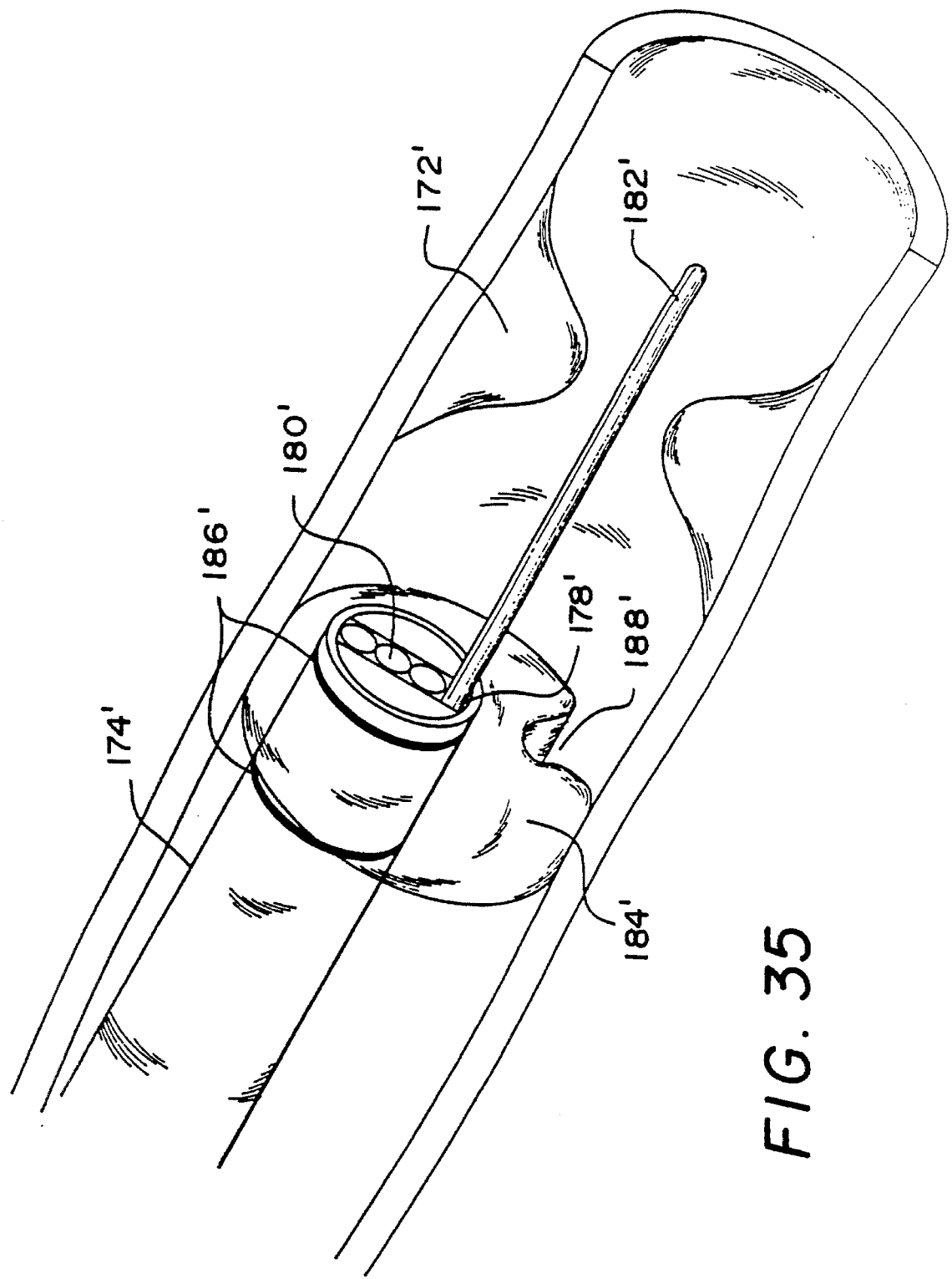
FIG. 35 is a perspective view of an alternative embodiment.

With reference to FIG. 35, a catheter 174' is disclosed that is substantially the same as the catheter 174 of FIG. 34, described above. The significant difference between the catheter 174 of FIG. 34 and the catheter 174' of FIG. 35 is that the balloon 184' of FIG. 35 includes a recess 188' that enables blood to flow around the balloon 184' during its use.

The off-center balloon catheters of the present invention function differently from other balloon catheters that are used in interventional cardiology and radiology. The off-center balloon catheters of the present invention are not dilation devices, such as those used in Percutaneous Transluminal Angioplasty (PTA) and Percutaneous Transluminal Coronary Angioplasty (PTCA). They are not intended to laterally dilate the blood vessels in which they are used or to press a catheter against the wall of a vessel. They also are not intended to stop the flow of blood and replace it with saline, as is commonly done to improve visualization during angioscopy. Rather, they function as positioning devices which enable the optical fibers, and hence the high energy laser, to be precisely positioned within the blood vessel. In this regard, they are not intended to contact the walls of the blood vessel tightly, so that translation and/or rotation of the catheter is possible while the balloons are inflated, to thereby provide a mobile angioplasty operation.

Figure 36:
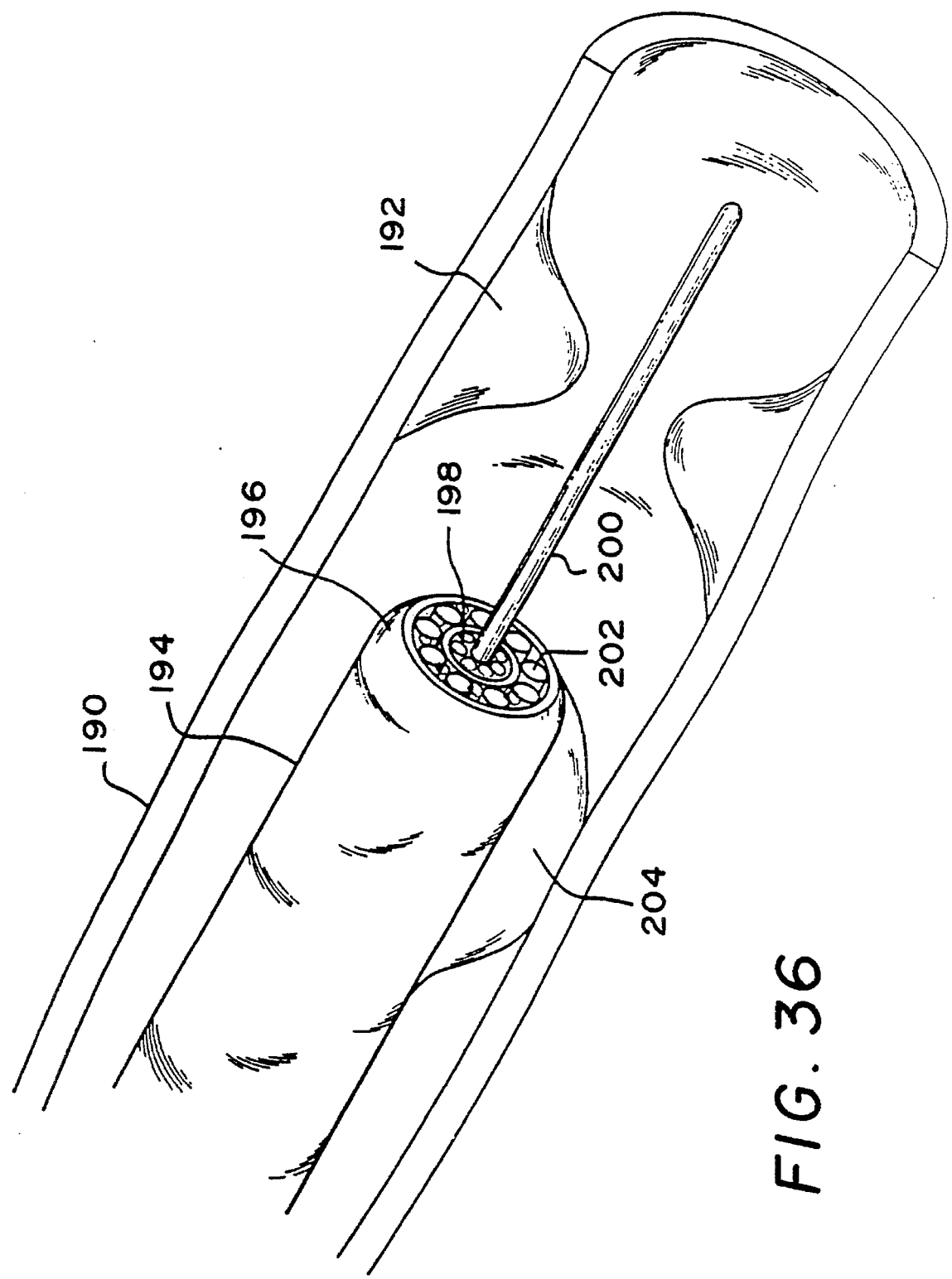
FIG. 36 is a perspective view of another alternative embodiment of a multilumen catheter.

With reference to FIG. 36, another embodiment of the present invention is illustrated within a blood vessel 190 having a lesion 192 therein. A catheter 194 has a smooth, rounded leading edge 196, which may be lubricous, e.g., coated with a water repellant chemical, for easy advancing and/or rotation through a blood vessel.

In the center of the catheter 194 is a guidewire lumen 198, within which lumen a guidewire 200 is slidably disposed. Surrounding the central guidewire lumen 198 is an annular array of optical fibers 202 that may be used to deliver high energy pulsed laser for ablating the lesion 192. A balloon 204 is mounted to a location on the outer periphery of the catheter 194.

In operation, the guidewire 200 is first threaded through the blood vessel 190 until it is adjacent the lesion 192. The catheter 194 is then conveyed along the guidewire 200 with the balloon 204 deflated until the catheter 194 is adjacent the lesion 192. At that point, a channel is ablated in the lesion 192 with laser energy delivered by the optical fibers 202. The size of the channel is substantially equal to the outside diameter of the catheter 194. The balloon 204 is then inflated, thus shifting the optical fibers 202 to a higher orbit. The lesion 192 is again ablated by the optical fibers 202 while advancing and/or rotating the catheter, thus forming a larger opening within the lesion 192. The balloon 204 may be further inflated, and the process repeated, as necessary.

As a result of the embodiment disclosed in FIG. 36, the lesion 192 is uniformly ablated by a plurality of optical fibers 202. As a result, the likelihood of large segments of the lesion 192 being released into the blood flow, where they may cause emboli down stream is substantially reduced. Because the lesion 192 is broken into small segments, there is no need to have a dedicated channel in the catheter to remove debris. The system disclosed in FIG. 36 generally creates particles less than 10 g in diameter.

Figure 37:
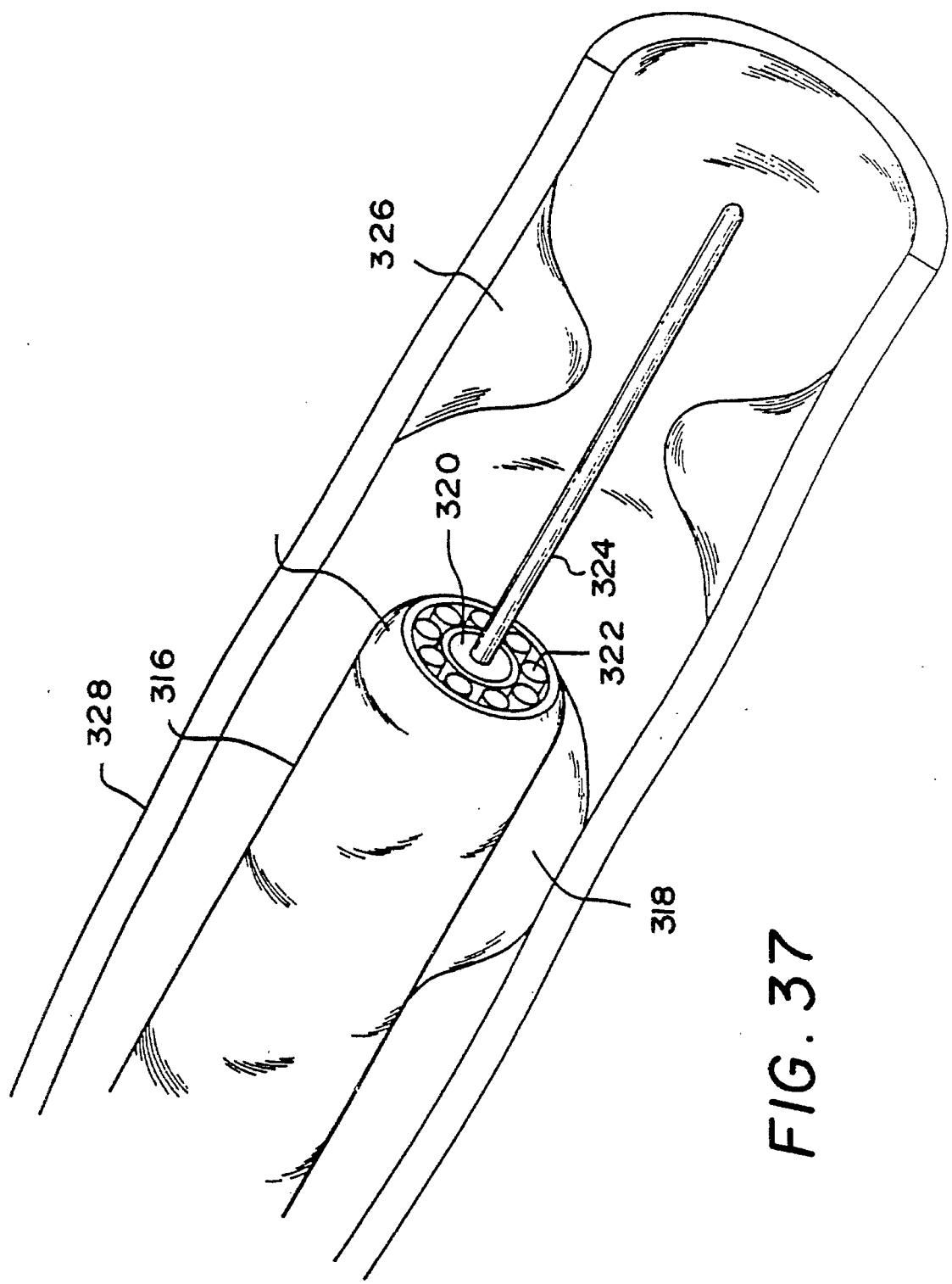
FIG. 37 is a perspective view of another alternative embodiment of a fiber optic catheter.

A further refinement of the catheter system disclosed in FIG. 36 is disclosed in FIG. 37. An outer catheter 316 includes an outer lumen or passage (not shown) for retaining means for inflating the balloon 318. An internal catheter 320 includes a plurality of optical fibers 322 and is slidable in an axial direction with respect to the outer catheter 316. The internal catheter 320 further includes a central lumen for a guidewire 324.

In use, the outer catheter 316 and internal catheter 320 are advanced together along the guidewire 324 to a lesion 326 in a vessel 328. At the location of the lesion 326, the balloon 318 is inflated to lock the outer catheter 316 in place within the vessel 328. The internal catheter 320 can then be advanced as desired while ablating the lesion.

Figure 38:
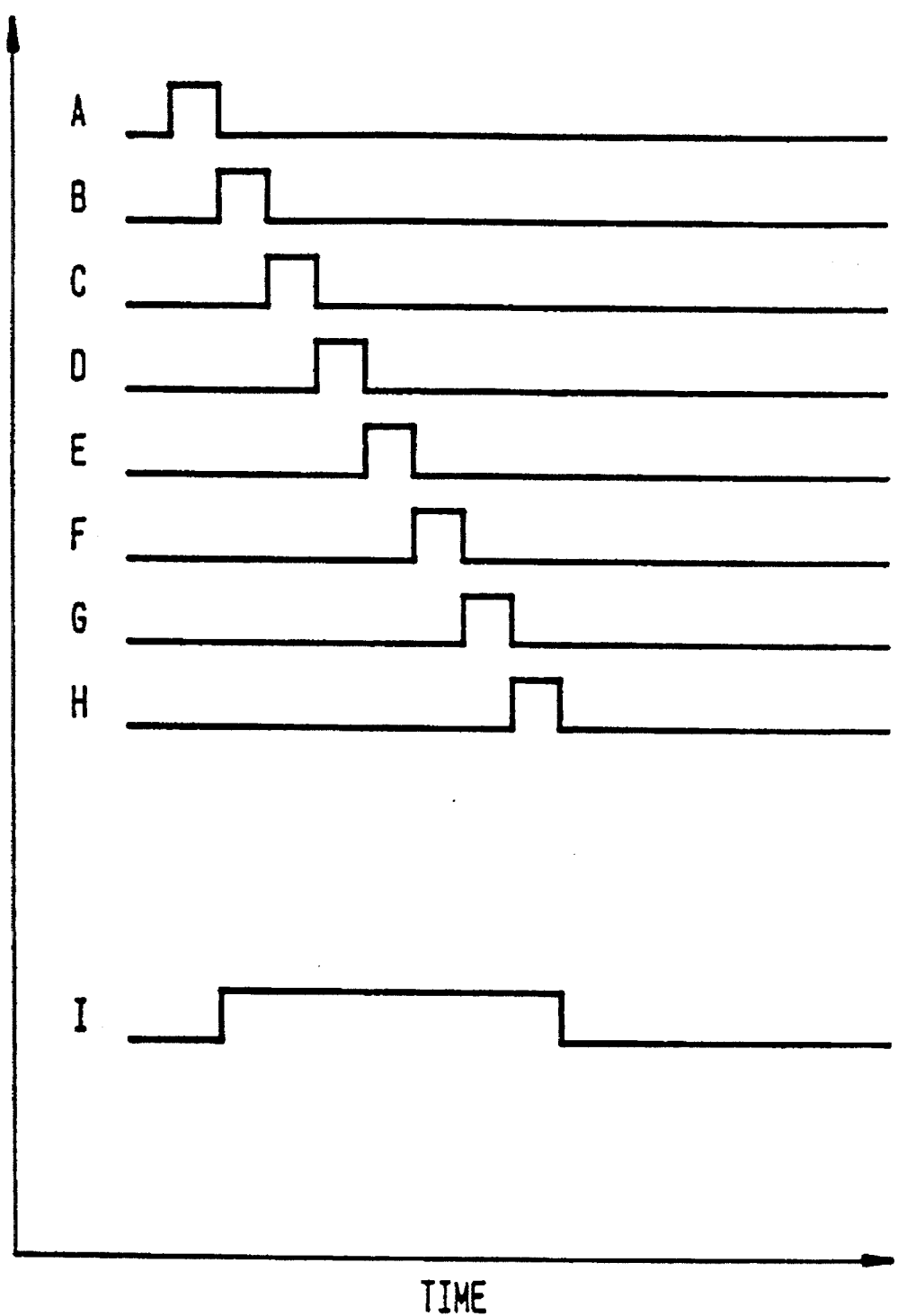
FIG. 38 is a graph showing pulse construction.

FIG. 38 relates to a method of transmitting high energy pulsed laser beams through a substantially pure silica fiber. FIG. 38 depicts a pulse that is made up of a train or a group of time shifted subpulses. A high energy long pulse I is a super positioning of numerous subpulses A–H and has a shorter diffusivity of tissue. In other words, a high energy pulse duration can be stretched in time when ablating a tissue without causing undesired thermal damage to adjacent tissue due to the thermal diffusion through the tissue during the ablation process. The estimated time needed to move a high energy laser pulse from an ablation zone tissue is about one millisecond.

U.S. Pat. No. 4,677,636 relates to such laser pulses, and the subject matter thereof is incorporated herein by reference.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A deflectable catheter having a distal tip and a proximal end, comprising:

a fiber optic core extending from the distal tip of the catheter to the proximal end thereof;

hollow means for encasing said core;

said hollow means including a deflecting region;

said core being fixed to said hollow means at a distal end of said deflecting region; and control means mounted at proximal end of said core and said hollow means for applying a tension to said core so as to cause deflection of the deflecting region;

said fiber optic core being fixed to the distal tip of the catheter so as to permit laser energy to be emitted in a forward direction of the catheter.

2. The deflectable carrier of claim 1, wherein said control means includes means for applying tension to the core.

3. A deflectable catheter having a distal tip and a proximal end, comprising:

a fiber optic core that includes a plurality of optical fibers;

said core being fixed to the distal tip of the catheter and extending to the proximal end thereof so as to convey laser energy from the proximal end of the catheter and emit the laser energy from the distal tip in a forward direction;

said optical fibers being arranged in rows, wherein each row is twisted in a direction that is opposite to a direction of adjacent rows;

hollow means for encasing said core;

said hollow means including a deflecting region, said deflecting region having a first side and a second side, said first side being on an opposite side of a plane extending axially through said hollow means than said second side;

said first side of said deflecting region being more compressible than said second side of said deflecting region;

said core being fixed to said hollow means at a distal end of said deflecting region; and control means mounted at the proximal end of said core and said hollow means for applying tension to said core with respect to said hollow means so that said tension causes said first side of said deflecting region to compress a greater amount than said second side, thus deflecting the deflecting region.

4. The deflectable catheter of claim 3, wherein a portion of said hollow means that includes said deflecting region is comprised of a wire coil.

5. The deflectable catheter of claim 3, further comprising a source of ultraviolet pulsed laser energy, wherein each pulse has a duration in a range of 10–3000 nsec, said source being coupled to a proximal end of said fiber optic core.

6. A deflectable catheter having a distal tip and a proximal end, comprising:

a fiber optic core extending from the distal tip of the catheter to the proximal end thereof;

hollow means for encasing said core;

said hollow means including a deflecting region, said deflecting region having a first side and a second side, said first side being on an opposite side of a plane extending axially through said hollow means than said second side;

said first side of said deflecting region being more compressible than said second side of said deflecting region;

said core being fixed to said hollow means at a distal end of said deflecting region; and control means mounted at it proximal end of said core and said hollow means for applying tension to said core with respect to said hollow means so that said tension causes said first side of said deflecting region to compress a greater amount than said second side, thus deflecting the deflecting region;

said fiber optic core being fixed to the distal tip of the catheter so as to permit laser energy to be emitted in a forward direction of the catheter.

7. The deflectable catheter of claim 6, wherein the difference between an outer diameter of the core and an inner diameter of said hollow means is no larger than necessary to enable adequate bending of the deflecting region.

8. The deflectable catheter of claim 6, further comprising a source of ultraviolet pulsed laser energy, wherein each pulse has an energy density of at least 50 mJ/mm$^2$ and a duration in a range of 10–3000 nsec, said source being coupled to a proximal end of said fiber optic core.

9. The deflectable catheter of claim 6, wherein the fiber optic core includes a plurality of optical fibers that are arranged such that bending stresses are substantially evenly distributed among the fibers when the catheter is bent.

10. The deflectable catheter of claim 6, wherein the fiber optic core includes a plurality of optical fibers that are all of the same approximate diameter.

11. The deflectable catheter of claim 6, wherein the fiber optic core includes a plurality of optical fibers that are approximately 50 microns in diameter.

12. The deflectable catheter of claim 6, further comprising a radiopaque marker band at the distal end of said catheter.

13. A deflectable catheter of claim 6, wherein the control means comprises:
   a first portion fixed to the core;
   a second portion fixed to the hollow means; and
   means for manipulating a relative position of the first and second portions in order to control the tension in the core.

14. The deflectable catheter of claim 13, wherein the first portion is a finger grip and the second portion is a thumb ring.

15. The deflectable catheter of claim 6, wherein the core includes a central optical fiber at a center thereof and a plurality of optical fibers thinner than said central optical fiber wrapped about the central optical fiber.

16. The deflectable catheter of claim 15, wherein the optical fibers are arranged in rows, and each row is wound in a direction that is opposite to a direction of adjacent rows.

17. The deflectable catheter of claim 6, further comprising ultrasound sensors arranged at the distal end of the catheter.

18. The deflectable catheter of claim 17, wherein said ultrasound sensors are fixed so as to sense the distance radially from said catheter to a wall of a vessel in which the catheter is being used.

19. The deflectable carrier of claim 6, wherein a portion of said hollow means that includes said deflecting region is comprised of a wire coil.

20. The deflectable carrier of claim 19, wherein the diameter of the wire on the first side is smaller than the diameter of the wire on the second side.

21. The deflectable carrier of claim 19, wherein a wire of the wire coil has a nonuniform cross section such that a distance between opposing edges of adjacent wire coils is greater on the first side than on the second side.

22. The deflectable carrier of claim 21, wherein the wire of the wire coil is mechanically deformed on the first side so that a cross section of the wire on the first side is noncircular.

23. A deflectable catheter having a distal tip and a proximal end, comprising:
   a fiber optic core having an outer diameter and extending from the distal tip of the catheter to the proximal end thereof;
   hollow means having an inner diameter for encasing said core;
   said hollow means including a deflecting region;
   said core being fixed to said hollow means at a distal end of said deflecting region;
   control means mounted at a proximal end of said core and said hollow means for applying a tension to said core so as to cause deflection of the deflecting region; and
   said fiber optic core being exposed at a distal tip of the core so as to permit emission of laser energy in a forward direction; and
   wherein a difference between the outer diameter of the core and the inner diameter of the hollow means enables adequate bending of the deflecting region and enables the core to provide support for the hollow means during deflection of the hollow means.

24. The deflectable catheter of claim 23, wherein the fiber optic core comprises a plurality of optical fibers that are arranged in rows, and each row is twisted in a direction that is opposite to a direction of adjacent rows.

25. The deflectable catheter of claim 23, further comprising a source of ultraviolet pulsed laser energy, wherein each pulse has an energy density of at least 50 mJ/mm$^2$ at a proximal end of said catheter and a duration in a range of 10–3000 nsec, said source being coupled to a proximal end of said fiber optic core.

26. The deflectable catheter of claim 23, wherein the fiber optic core includes a plurality of optical fibers that are arranged such that bending stresses are substantially evenly distributed among the fibers when the catheter is bent.

* * * * *